United States Patent [19]

Brooker et al.

[11] Patent Number: 5,332,905
[45] Date of Patent: Jul. 26, 1994

[54] APPARATUS AND METHOD FOR MULTIPLE EMISSION RATIO PHOTOMETRY AND MULTIPLE EMISSION RATIO IMAGING

[75] Inventors: Gary Brooker, Potomac; J. Scott McDonald, Germantown, both of Md.; Jeffrey S. Brooker, Herndon, Va.

[73] Assignee: Atto Instruments, Inc., Rockville, Md.

[21] Appl. No.: 935,873

[22] Filed: Aug. 26, 1992

[51] Int. Cl.$^5$ ............................................. G01N 21/64
[52] U.S. Cl. ............................ 250/458.1; 250/459.1; 250/361 C; 356/417
[58] Field of Search ............ 250/458.1, 459.1, 371 C; 356/317, 417

[56] References Cited

U.S. PATENT DOCUMENTS

| | | | |
|---|---|---|---|
| 4,808,828 | 2/1989 | Kitamori et al. | 250/458.1 |
| 5,102,625 | 4/1992 | Milo | 250/458.1 |
| 5,149,972 | 9/1992 | Fay et al. | 250/461.1 |
| 5,166,813 | 11/1992 | Metz | 250/459.1 |
| 5,173,432 | 12/1992 | Lefkowitz et al. | 250/459.1 |
| 5,212,386 | 5/1993 | Gratton et al. | 250/459.1 |

OTHER PUBLICATIONS

Paul J. Sammak et al., "Intracellular Cyclic AMP, Not Calcium, Determines the Direction of Vesicle Movement in Melanophores: Direct Measurement by Fluoroescence Ratio Imaging," Journal of Cell Biology (Apr. 1992).
Maria A. Debernardi et al., "Inhibition of cAMP Accumulation by Intracellular Calcium Mobilization in C6-28 Cells Stably Transfected with Substance K Receptor cDNA," Proc Natl. Acad. Sci. USA, vol. 88, pp. 9257-9261 (Oct. 1991).
Hong Zhang et al., "Sphingosine-1-Phosphate, A Novel Lipid, Involved in Cellular Proliferation," The Journal of Cell Biology, vol. 114, No. 1, pp. 155-167 (Jul. 1991).
Stephen R. Adams et al., "Fluroescence Ratio Imaging of Cyclic AMP in Single Cells," Nature, vol. 349, pp. 694-697 (Feb. 21, 1991).
Gabriel A. De Erausquin et al., "Ganglioside Normalize Distorted Single—Cell Intracellular Free CA$^{2+}$ Dynamics After Toxic Doses of Glutamate in Cerebellar Granule Cells," Proc. Natl. Acad. Sci. USA, vol. 87, pp. 8017-8021 (Oct. 1990).
Gary Brooker et al., "Calcium Wave Evoked by Activation of Endogenous or Exogenously Expressed Receptors in Exnopus Oocytes," Proc. Natl. Acad. Sci. USA, vol. 87, pp. 2813-2817 (Apr. 1990).
R. Y. Tesi et al., "Practical Design Criteria for a Dynamic Ratio Imaging System," Cell Calcium, vol. 11, pp. 93-109 (1990).
Haruo Miyata et al., "Dual Loading of the Fluorescent Indicator Fura-2 and 2,7-Biscarboxyethyl-5(6)-Carboxyfluorescein (BCECF) in Isolated Myocytes," Biochem. Biophy. Res. Comm., vol. 163, No. 1, pp. 500-505 (1989).
Catalog, Molecular Probes, Inc.; pp. 86-94 (undated).
Attofluor Operation Manual, pp. 3-11.
Sales Invoice, Dated Aug. 28, 1991, For Attofluor Ratio Imaging System.

*Primary Examiner*—Paul M. Dzierzynski
*Assistant Examiner*—Drew A. Dunn
*Attorney, Agent, or Firm*—Oblon, Spivak, McClelland, Maier & Neustadt

[57] ABSTRACT

The concentration of at least one luminescence-affecting chemical species in at least one location in a sample capable of emitting luminescent radiation can be determined using multiple luminescent emission ratio photometry and multiple luminescent emission ratio imaging. An apparatus and method for conducting multiple luminescent emission ratio photometry and imaging is provided.

16 Claims, 13 Drawing Sheets

EXCITATION FLOURESCENCE OF FURA-2 IN THE
ABSCENCE AND PRESENCE OF CALCIUM

EMISSION FLOURESCENCE OF INDO-1 IN THE
ABSCENCE AND PRESENCE OF CALCIUM

APPARATUS AND METHOD FOR MULTIPLE EMISSION RATIO PHOTOMETRY AND MULTIPLE EMISSION RATIO IMAGING

BACKGROUND OF THE INVENTION

1. Field of the Invention

The present invention concerns an apparatus and a method for determining the concentration of one or more chemical species in a sample by multiple luminescent emission spectrophotometric ratios, and particularly, for producing an image of the sample relating concentration of the chemical species to location in the sample.

2. Discussion of the Background

Monitoring radiative emission phenomena, such as photoluminescence (e.g., fluorescence and/or phosphorescence), as a means of determining the presence, quantity and/or concentration of a particular chemical substance in a particular sample is a well-known technique in the chemical and biochemical arts. Radiative emission phenomena occur from absorption of radiative energy (e.g., infrared, visible or ultraviolet light, x-rays, etc.) by a chemical species, which in turn, reaches an electronically excited state. In relaxing to the ground state, radiative energy is emitted by the electronically excited chemical species (e.g., infrared or visible light, etc.). Alternatively, the electronically excited chemical compound relaxes by transferring energy to a second chemical species, which in turn, emits radiative energy. In photoluminescence, relatively high-energy photons are absorbed by a compound. In turn, the electronically excited compound emits photons at a lower energy.

A chemical substance has unique radiative emission spectra that are used to characterize the substance. A photoluminescence spectrum can measure either (1) the intensity of luminescent emission at a constant emission wavelength as a function of excitation wavelength (an "excitation" spectrum) or (2) the intensity of luminescent emission at a constant excitation wavelength as a function of emission wavelength (an "emission" spectrum). For example, In an excitation spectrum, the emission intensity of a luminescent compound will exhibit characteristic maxima and minima at particular excitation wavelengths. Similarly, in an emission spectrum, the emission intensity of a luminescent compound will exhibit characteristic maxima and minima at particular emission wavelengths.

Often, the radiative emission spectra of a given chemical species are influenced by the interaction of the species with a second species present in its environment. For example, pH or the presence of metal ions can affect the energies and intensities at which a fluorescent chemical species absorbs and emits radiative energy. The changes in energies and intensities at which a given chemical species emits radiative energy can provide information concerning the second species with which it interacts.

A luminescent compound in an essentially pure solvent (e.g., deionized water) will luminesce in a characteristic manner. However, at a different pH, for example, the compound will interact to a different extent with either protons or hydroxide ions, respectively, depending on whether the solution becomes more acidic or more basic. As a result of the change in the interaction of the compound with either protons or hydroxide ions, the luminescent behavior of the compound may also change.

One can measure the fluorescence or phosphorescence intensity of a sample containing the luminescent species as either a function of excitation wavelength or emission wavelength, then take identical measurements of the luminescent compound in the presence of known concentrations of a second species which interacts with the luminescent compound and influences its luminescent behavior. From solutions of known concentrations of the compounds, one can empirically determine relationships between the intensity of a luminescent compound at a given wavelength and the relative concentration of a second, luminescence-affecting species.

In a given sample, concentrations of both the luminescent compound and the second, luminescence-affecting species may be unknown or unevenly distributed. Some locations in the sample may have high concentrations of the luminescent compound, while other locations have low concentrations. If the concentration of the second species is distributed in the sample differently from the luminescent compound, the luminescence intensity alone cannot provide information concerning the concentration of the second species.

Luminescence intensity is dependent on the amount or concentration of the luminescent species, in the absence of a second species which affects its luminescence behavior. In the presence of such a second species, the luminescence intensity is-affected in a manner proportional to the concentration of the second, luminescence-affecting species. As a result (for example, when the second species directly affects the intensity of the luminescent species), the locations in the sample having high concentrations of the luminescent compound and very high concentrations of the second species may luminesce at a given wavelength with roughly the same intensity as other locations having low concentrations of the luminescent compound and very low concentrations of the second species, if the concentration of the species at the particular emission wavelength being monitored (either the free luminescent compound or the interacting luminescent compound-second species complex) is the same. On the other hand, if the intensity of the luminescent species is inversely affected by the second species, locations in the sample having high concentrations of the luminescent compound and low concentrations of the second species could show the same intensity at a particular wavelength as locations having low concentrations of the luminescent compound and high concentrations of the second species. As a result, false determinations of the concentration of the second species result from determining the intensity of the luminescent compound at one wavelength, when the concentration of the luminescent compound is not known or the concentration distribution in the sample can vary.

This problem can be overcome by choosing two wavelengths of either emission or excitation, wherein at one wavelength, the luminescent compound exhibits a relatively high intensity, but in the presence of the second, luminescence-affecting species, exhibits a relatively low intensity; and at the other wavelength, the luminescent compound exhibits a relatively low intensity, but in the presence of the second, luminescence-affecting species, exhibits a relatively high intensity. Thus, by measuring the intensity at each of two wavelengths of either emission or excitation at which the luminescence intensity shows a strong dependance on the concentration of the second, luminescence-affecting species, one can compare the two measurements and determine the extent of the influence of the second species on the luminescence of the luminescent compound.

If one divides the intensity at the first wavelength by the intensity at the second wavelength for solutions of known concentrations of the luminescent compound and varying concentrations of the second species, one obtains a ratio of intensity in which the dependence on the concentration of the luminescent compound cancels out. Thus, one can obtain characteristic data for the concentration-dependant influence of the second species independent of the concentration of the luminescent species. Accordingly, for a sample containing a luminescent compound and a second, luminescence-affecting species, the ratio of the luminescence intensity at one wavelength of either emission or excitation to the luminescence intensity at a second wavelength, when compared to the ratios at the same wavelengths of samples of the two species at known concentrations, provides information about the concentration of the second species throughout the sample which would otherwise be difficult or impossible to obtain.

By dividing the sample into a large number of detection areas and measuring the intensity ratios of the sample in each of the areas, one can produce an image which correlates the concentration of a second, luminescence-affecting species to locations in the sample. In the biochemical arts, fluorescence ratio imaging is becoming a widely used technique. For example, fluorescence ratio imaging has been successfully employed in the analysis of calcium ions in living cells (Brooker et al, *Proc. Natl. Acad. Sci. USA*, 87:2813–2817 (1990); Tsien et al, *Cell Calcium*, 11:93–109 (1990); de Erausquin et al, *Proc. Natl. Acad. Sci. USA*, 87:8017–8021 (1990); DeBernardi et al, *Proc. Natl. Acad. Sci. USA*, 88:9257–9261 (1991); Zhang et al, *J. Cell Biol.*, 114:155–167 (1991)).

The general procedure in fluorescence ratio imaging (or "fluorescence ratioing") is to first measure the fluorescence intensity of a subject at two distinct wavelengths of either emission or excitation radiation, determine the ratio of the intensity at one wavelength to the intensity at the other wavelength for each location or "point" in the sample, and then print a subsequent two-dimensional image of the sample having characteristics of a third dimension (e.g., color) as a function of the value of the ratio (the ratio image). As described above, the ratio image provides information about the concentration of the interacting species (e.g., calcium) at various locations in the subject (e.g., living cells). The advantage of the two wavelength-two image approach on the same sample is that the ratio of the fluorescence intensities of the two images is purely a function of calcium ion, independent of fluorescent dye distribution within the cell, which may be uneven. (Of course, in areas where the concentration of the luminescent species is zero, no information can be obtained concerning the second species. However, this problem also exists in methods not based on ratioing.)

The dye Fura-2 is a calcium chelator that emits quantitatively different fluorescence spectra at different excitation wavelengths as a function of the concentration of free calcium ion. In the presence of a high concentration of calcium ion, Fura-2 fluoresces brightly (at high intensity) when excited at 340 nm and dimly (at low intensity) when excited at 380 nm. In the presence of a low concentration of calcium ion, the fluorescence intensities at 340 and 380 nm are reversed (dim when excited at 340 nm and bright when excited at 380 nm).

Because Fura-2 is excited at two different wavelengths, and the fluorescence emission is monitored at the same wavelength band (generally >500 nm), it is considered a "dual excitation/single emission" dye. The reversal of its fluorescence characteristics in response to calcium concentration is the key to fluorescence ratio imaging using Fura-2. A theoretical depiction of the fluorescence characteristics of Fura-2 are shown graphically in FIG. 1.

Another characteristic of Fura-2 that should be noted from FIG. 1 is that the emission of Fura-2 is the same at any calcium concentration when excited at a wavelength of 360 nm. This is the isobestic point for Fura-2, or the wavelength of excitation where fluorescence is independent of calcium concentration. This property can thus be used to determine the distribution of Fura-2 within a specimen, or to measure the amount of Fura-2 at any point or location within a sample.

Fura-2 can be unevenly distributed within a cell or sample (field) of cells. The use of a ratio image (created from the ratio of two individual images) to view calcium ion distribution within a cell mathematically eliminates the variation in spatial dye distribution, since the dye concentration appears in both the numerator and denominator of the ratio, and thus, is cancelled out. Therefore, within reasonable limits, uneven distribution of dye within a specimen does not affect the validity of calcium concentration readings, since calcium concentration is a function of only the ratio of the intensity of the fluorescence of the two respective images taken at 340 nm and 380 nm. The mathematical relationship is shown in the following equation:

$$[Ca^{++}] = Kd\left[\frac{R - R(Lo)}{R(Hi) - R}\right]\frac{380(Lo)}{380(Hi)}$$

wherein:
R(Lo) = the ratio of the emission intensity at 340 nm excitation to the emission intensity at 380 nm excitation at a $Ca^{++}$ concentration of zero R(Hi) = the ratio of the emission intensity at 340 nm excitation to the emission intensity at 380 nm excitation at $Ca^{++}$ saturation 380(Lo) = the emission intensity at 380 nm excitation at a $Ca^{++}$ concentration of zero 380(Hi) = the emission intensity at 380 nm excitation at $Ca^{++}$ saturation Kd = dissociation constant of the $Ca^{2+}$--Fura complex in nM R = the experimentally determined 340/380 intensity ratio Thus, the standardization data for R(Lo), R(Hi), 380(Lo) and 380(Hi) need to be obtained by viewing Fura-2 solutions containing zero and saturating concentrations of calcium. This data is then included in the ratio calculations for construction of a standard curve relating calcium concentration to the 340/380 intensity ratio (R).

Indo-1 is another fluorescent dye that exhibits calcium concentration-dependent luminescent behavior. Indo-1 is similar to Fura-2 in that its emission response to radiant excitation energy is dependent upon calcium, but Indo-1 is a single-excitation/dual-emission dye.

When excited at a wavelength of 340-360 nm in the presence of a high concentration of calcium, Indo-1 emits brightly at 420 nm and emits dimly at 500 nm. In the presence of a low concentration of calcium, Indo-1 has a low fluorescence intensity at 420 nm and a high fluorescence intensity at 500 nm. The graphs for Indo-1 fluorescence look similar to those for Fura-2, except that the x-axis is changed to represent emission wavelength rather than excitation wavelength. A theoretical depiction of the fluorescence characteristics of Indo-1 are shown graphically in FIG. 2.

By monitoring the fluorescence ratio image as a function of time of a sample containing either Fura-2 or Indo-1, one can analyze time-dependent phenomena concerning the chemical species of interest (e.g., the movement of $Ca^{2+}$ across cell membranes or in response to certain biochemical stimuli). Hence, fluorescence ratio imaging has become a useful technique for monitoring the amount of a chemical species which exhibits concentration-dependent effects on the luminescence of a luminescent compound.

Imaging more than one emission ratio would permit one to draw a direct relationship between the luminescence-affecting species being monitored. By imaging essentially simultaneous multiple emission ratios on the same sample, a built-in control is provided, and the variable factors which differ between samples and the errors which inevitably occur in conducting non-concurrent experiments can be eliminated.

However, one who wishes to monitor more than one emission ratio in the same sample or substrate has been unable to do so using prior technology. Prior to the present invention, the state of available instrumentation permitted only the monitoring of a single emission intensity ratio, due to limitations with regard to the number of luminescent emissions which could accurately be monitored by the same instrument (limited to a maximum of 2).

Attempts to monitor more than one ratio using prior technology have had to rely on techniques such as employing multiple neutral density filters on a filter wheel positioned between the sample and the detector, or alternatively, changing the source of excitation energy either by multiple filters or by actually changing the source itself. These approaches introduce fatal errors, because the sample mount either had to be removed in order to change the appropriate piece of equipment, or if automatic changers were used, vibrations sufficient to jar the sample mount and alter the visual field resulted. Furthermore, use of multiple filters or multiple excitation energy sources in conjunction with a detector having the capability of monitoring only two emission phenomena limits the range of sensitivity for additional sets of emissions.

Furthermore, the maximum speed with which the prior instrument can switch back and forth between emission measurements at each of the wavelengths being monitored is about three switches per second (i.e., the prior instrument is limited to about three fluorescence measurements per second). Even with these limitations, the prior instrument is useful for monitoring phenomena associated with a single luminescence ratio which occur over the course of from several seconds to several hours or more.

Prior to the present invention, to conduct multiple emission ratioing, one would have to conduct separate experiments for each fluorescent substance to be monitored, because the filter controlling the wavelength of excitation light must be changed to monitor the second emission. Alternatively, even if one is able to employ a source of four wavelengths of radiation, one can monitor only two emission phenomena using prior technology, since prior detectors are limited to monitoring only two emissions without having to recalibrate the detector for reliable measurements of additional emissions. Therefore, one would have to recalibrate the detector for the emissions corresponding to the second fluorescent substance after measuring the two emissions of the first fluorescent substance, in order to monitor the ratio for the second fluorescent substance.

For example, de Erausquin et al (*Proc. Natl. Acad. Sci USA*, 87:8017-8021 (1990)) determined, for the same sample of cells, calcium concentration by fluorescence ratio imaging and cell viability by qualitative propidium iodide fluorescence. However, after taking the measurements for producing the calcium concentration fluorescence ratio image, de Erausquin et al required about 1 h. 45 min. to take the qualitative propidium iodide fluorescence measurements. It should also be noted that qualitative propidium iodide fluorescence to test cell viability does not involve ratioing, but rather, merely involves detection of propidium iodide fluorescence in the cell nucleus.

In any case, the procedures for imaging more than one luminescent ratio are time-consuming using prior instrumentation, and would prevent one from being able to monitor phenomena which occur on a time scale of less than about an hour or two.

If the procedures are carried out flawlessly, changing filters on a typical device for monitoring a fluorescence ratio (e.g., an inverted microscope) takes at least 5-10 minutes, and recalibrating a typical single-ratio detector takes about 10-15 minutes. Attempting to conduct multiple emission ratioing on the same sample prevents one from monitoring the concentration of a given substance with respect to time for phenomena which occur on a time scale of from several seconds to several minutes. Thus, the possibility of simultaneously monitoring many important functions of cellular physiology and biochemical behavior is precluded using prior technology.

SUMMARY OF THE INVENTION

Accordingly, one object of the present invention is to provide a novel method for determining the concentrations of at least two luminescence-affecting chemical species in a sample exhibiting concentration-dependent luminescent phenomena by measuring at least two independent luminescent emissions of each one of the luminescent substances within a period of time of from about one microsecond to about one minute.

A further object of the present invention is to provide a novel method for determining the concentrations of at least two fluorescence-affecting chemical species in a sample exhibiting concentration-dependent fluorescent phenomena by measuring at least two independent fluorescent emissions of each one of the fluorescent substances within a period of time of from about one microsecond to one minute.

A further object of the present invention is to provide a novel method for producing at least one image of the concentrations of each of at least two luminescence-affecting substances in a sample by multiple emission ratio imaging.

A further object of the present invention is to provide a novel method for producing at least two images of the concentrations of at least two fluorescence-affecting substances in a sample by multiple emission ratio imaging.

A further object of the present invention is to provide a novel apparatus for determining the concentrations of at least two luminescence-affecting chemical species in a sample exhibiting concentration-dependent luminescent phenomena having means to measure at least two independent luminescent emissions of each one of the luminescent substances within a period of time of from about one microsecond to one minute.

A further object of the present invention is to provide a novel apparatus for determining the concentrations of at least two fluorescence-affecting chemical species in a sample exhibiting concentration-dependent fluorescent phenomena having means to measure at least two independent fluorescent emissions of each one of the fluorescent substances within a period of time of from about one microsecond to one minute.

A further object of the present invention is to provide a novel apparatus for producing at least one image of the concentrations of each of at least two luminescence-affecting substances in a sample by multiple emission ratio imaging.

A further object of the present invention is to provide a novel method for producing at least two images of the concentrations of at least two fluorescence-affecting substances in a sample by multiple emission ratio imaging.

These and other objects which will become apparent during the following description of the drawings and of the preferred embodiments, are provided by an apparatus and a method for determining the concentration of at least two luminescence-affecting chemical species in a sample capable of emitting luminescent radiation, comprising the steps of:

(1) irradiating the sample with excitation radiation of sufficient energy to cause the sample to emit two pairs of independent luminescent emissions, each emission having an intensity, and for each one of the two pairs of independent luminescent emissions, each member of the pair having a common wavelength of excitation radiation or emission radiation and a different wavelength of the excitation radiation or emission radiation, such that when the common wavelength is excitation radiation, the different wavelength is emission radiation, and when the common wavelength is emission radiation, the different wavelength is excitation radiation, (2) measuring the intensity of each of the two pairs of independent luminescent emissions within a period of time of from about one microsecond to one minute, (3) determining, for each of the two pairs of independent luminescent emissions, a ratio of one of the luminescent radiation emission intensities of the pair to the remaining one of the luminescent radiation emission intensities of the pair, and (4) correlating each ratio to concentrations of each of the two luminescence-affecting chemical species in the sample.

BRIEF DESCRIPTION OF THE DRAWINGS

A more complete appreciation of the present invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
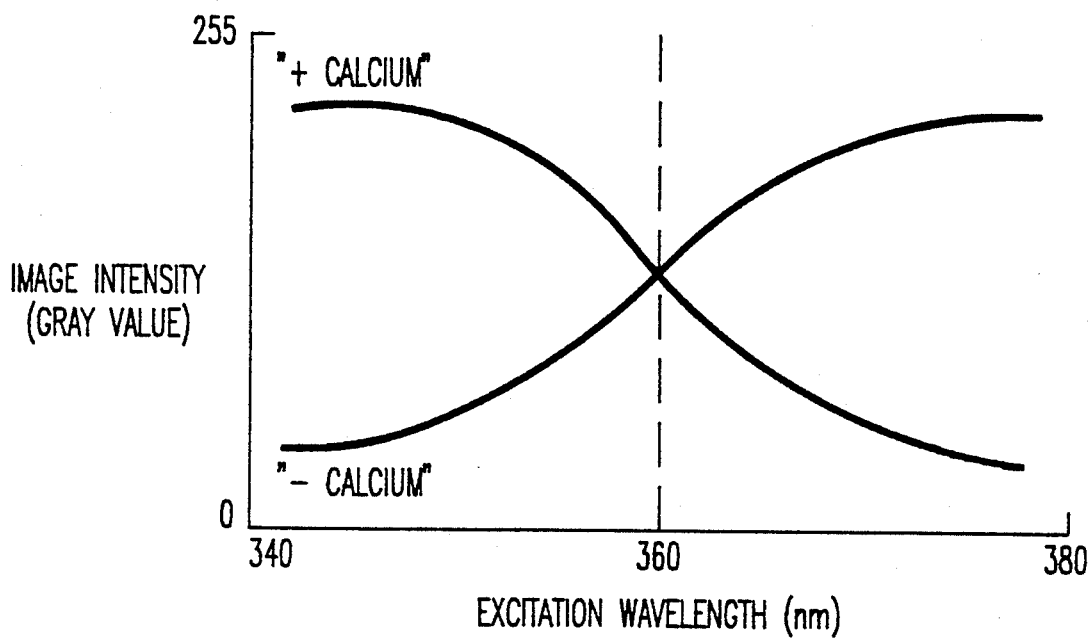
FIG. 1 graphically displays the theoretical fluorescence characteristics of Fura-2.
Figure 2:
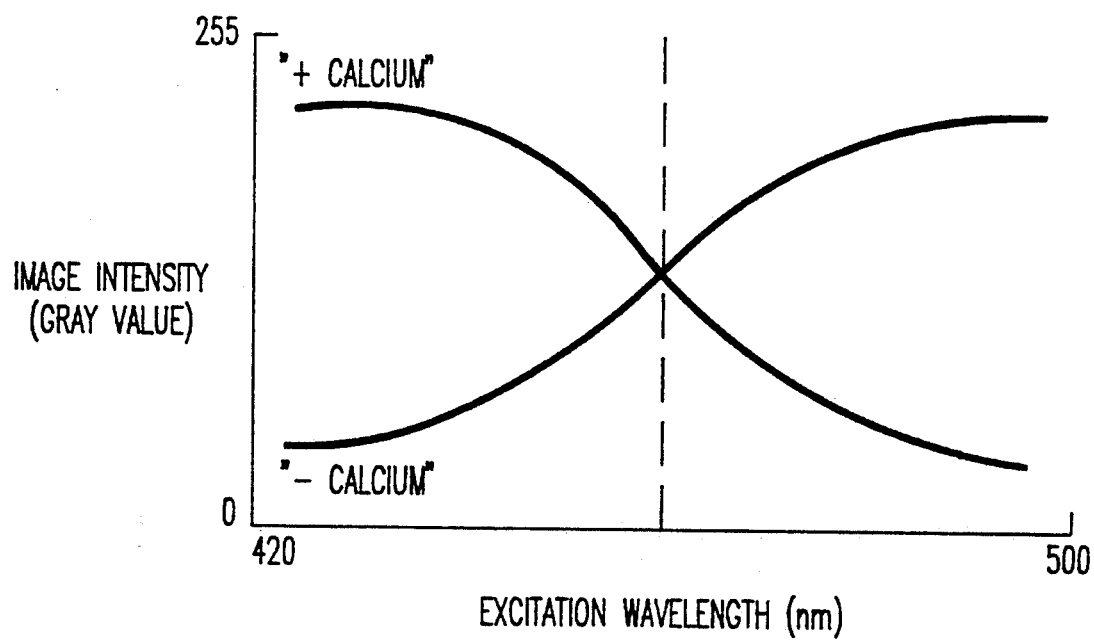
FIG. 2 graphically displays the theoretical fluorescence characteristics of Indo-1.
Figure 3:
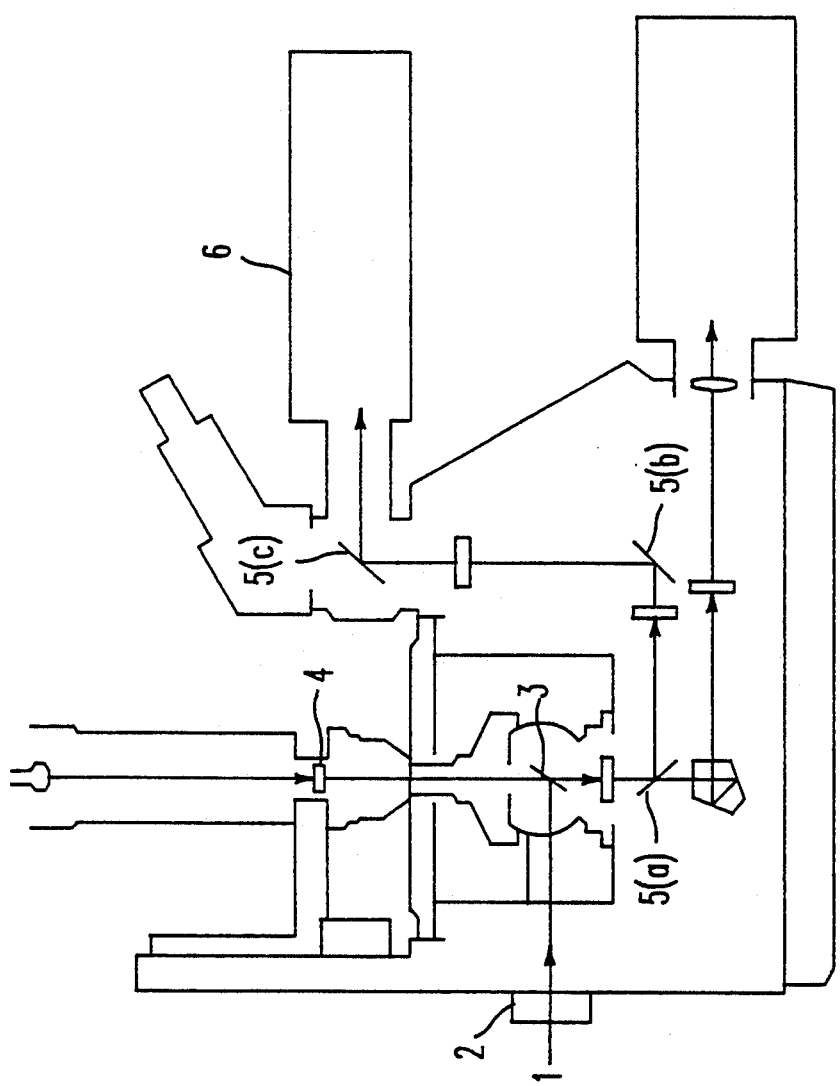
FIG. 3 is a side view of an inverted microscope useful for conducting multiple emission ratioing.

Referring now to the drawings, wherein like reference numerals designate identical or corresponding parts throughout the several views and more particularly to FIG. 3 thereof, light source 1 provides light of a suitable excitation energy to result in the desired emission phenomena. The light passes through filter 2, and is then reflected by dichroic mirror 3 towards the sample 4. The excitation light is then absorbed by a luminescent (fluorescent or phosphorescent) substance/luminescence-affecting species complex in the sample 4. The luminescent substance becomes excited, then emits light of a lower energy and longer wavelength than the excitation light. The light emitted from the luminescent substance passes through dichroic mirror 3, and is reflected by a series of mirrors 5(a), 5(b) and 5(c) to detector 6, where the emission is measured. The process is repeated to obtain a second emission for the first complex, then twice more for the second luminescent substance/luminescence-affecting species complex. Each of the four emissions is monitored independently.

As is understood in the art, the energy of light is inversely proportional to its wavelength. The terms "energy" and "wavelength" can be used interchangeably with regard to light. Further, the terms "luminescent" and "luminescence" refer to both fluorescent and phosphorescent phenomena.

The present invention particularly concerns a method for determining the concentration of at least two luminescence-affecting chemical species in a sample capable of emitting luminescent radiation, comprising the steps of:

(1) irradiating said sample with excitation radiation of sufficient energy to cause said sample to emit two pairs of independent luminescent emissions, each emission having an intensity, and for each one of said two pairs of independent luminescent emissions, each member of said pair having a common wavelength of excitation radiation or emission radiation and a different wavelength of the excitation radiation or emission radiation, such that when said common wavelength is excitation radiation, said different wavelength is emission radiation, and when said common wavelength is emission radiation, said different wavelength is excitation radiation, (2) measuring the intensity of each of said two pairs of independent luminescent emissions within a period of time of from about one microseconds to one minute, (3) determining, for each of said two pairs of independent luminescent emissions, a ratio of one of said luminescent radiation emission intensities of said pair to the remaining one of said luminescent radiation emission intensities of said pair, and (4) correlating each ratio to concentrations of each of said two luminescence-affecting chemical species in said sample.

Alternatively, the present process is adaptable to monitoring dual-excitation, dual-emission complexes. This alternative process comprises the steps of:

(1) irradiating a sample having a first luminescent substance/luminescence-affecting species complex and a second luminescent substance/luminescence-affecting species complex with excitation radiation of sufficient energy to cause each luminescent substance/luminescence-affecting species complex in the sample to emit a pair of independent luminescent emissions, each emission having an intensity, (2) measuring the intensity of each of the two pairs of independent luminescent emissions within a period of time of from about one microsecond to one minute, (3) determining, for each of the luminescent substance/luminescence-affecting species complexes, a ratio of one of the luminescent radiation emission intensities to the remaining one of the luminescent radiation emission intensities of the pair, and (4) correlating each ratio to concentrations of each of the two luminescence-affecting chemical species in the sample.

Preferably, the present method determines the concentration of at least two fluorescence-affecting chemical species. In the case of a dual-excitation, dual-emission complex, the excitation radiation of sufficient energy to cause each luminescent substance/luminescence-affecting species complex in the sample to emit a pair of independent luminescent emissions must be at different wavelengths for each complex. However, if one or both of the excitation energies for one dual-excitation, dual-emission complex overlaps with one or both of the excitation energies for another dual-excitation, dual-emission complex, the overlapping excitation energies must have different corresponding emission energies in order to be independent of each other. Further, the first luminescent substance/luminescence-affecting species complex in a sample may be dual-excitation, dual-emission, and the second may be either dual-excitation, single-emission or single-excitation, dual-emission.

Optionally, the method may further comprise the step of producing at least two images of the sample, each of the images showing the concentrations of each of the luminescence-affecting chemical species in the sample. The first ratio of the first pair of emissions is correlated to the concentration of a first luminescence-affecting chemical species, and the second ratio of the second pair of emissions is correlated to the concentration of a second luminescence-affecting chemical species, and so on for additional luminescence-affecting chemical species. The images are generally two-dimensional, with three-dimensional characteristics such as color, shading, brightness, etc., showing the concentration of the luminescence-affecting chemical species in the various locations of the sample. Alternatively, such a three-dimensional characteristic can be correlated to wavelength of excitation or emission energy, to provide information concerning wavelength-dependent luminescent phenomena.

Time-dependent luminescent phenomena are also of interest, and can be monitored by the present apparatus and method. Accordingly, the present method may further comprise repeating measuring step (2) within a period of time of from about one-third of a microsecond to about one minute of the completion of the first series of four independent emission intensity measurements. By continuously repeating measuring step (2), storing and processing the data gathered, and producing sequential images from the ratios determined, one can monitor and analyze dynamic changes in the concentrations of chemical species in a sample.

The present method is particularly suitable for fluorescence emission ratio concentration determinations on a sample containing biological cells, and for producing images of biological cell samples therefrom.

The apparatus of the present invention for producing multiple luminescence ratio images comprises:

(A) a light source providing a light beam of sufficient energy to electronically excite at least one luminescent compound in a sample, (B) a light filter positioned in the path of the light beam to filter out selected wavelengths of the light beam, (C) a dichroic mirror positioned in the path of the filtered light beam to reflect the filtered light beam in the direction of the sample, (D) a mounting platform for the sample positioned such that the reflected light beam strikes the sample so that the luminescent compound becomes electronically excited and produces luminescent emissions, and (E) a detector positioned to receive the reflected luminescent emissions and having an electronic switching device for adjusting the sensitivity of the detector at least four times within a period of time of from about one microsecond to one minute.

Optionally, one or more reflecting mirrors 5(a)–(c) as shown in FIG. 3 can be positioned to reflect the luminescent emissions from the sample, if the detector is not positioned to directly receive emissions from the sample (e.g., if the detector is not directly under an objective (lens element used to focus and view the sample). On the other hand, for example, the objective in an upright or inverted microscope is positioned to directly receive emission light from the sample and transmit it to the detector. An upright microscope employed in epifluorescence detection, where both excitation and emission energy are transmitted through the same objective, can be employed in the present process.

Preferably, the detector of the present apparatus comprises (a) a lens to intercept and focus the reflected luminescent emissions, (b) a camera equipped with a photosensitive element positioned to intercept the focused luminescent emissions, and (c) means for augmenting the electrical signals produced in the photosensitive element electronically connected between the photosensitive element and a data storage device (e.g., computer). In a preferred embodiment, the electronic switching device electronically connects the photosensitive element to a means for controlling the sensitivity of the photosensitive element (e.g., a computer having predetermined sensitivity settings for each independent emission being monitored).

In addition to conventional photosensitive elements in commercially available cameras, the detector can comprise four or more solid-state emission detectors having analog circuitry, capable of providing a direct current (DC) signal. Such solid-state emission detectors are capable of processing and sending data as quickly as it is received and/or generated, thus providing a means of continuous data acquisition and processing. The speed with which such solid-state emission detectors acquire and process data is limited only by sensitivity of the corresponding light detection device. Such solid-state emission detectors are particularly suitable for use in conjunction with lasers as excitation energy sources, or with laser-scanning microscopes in the study of microscopic samples, such as those containing biological cells.

Any light source which provides the desired intensities and energies of light sufficient to excite the luminescent compound(s) of interest are suitable for use in the present invention. Preferred light sources include xenon arc lamps, mercury arc vapor lamps and argon arc lamps, etc. The most preferred light source is a mercury burner.

However, for very high speed cycles of measurement (measurement steps and/or cycles of from about 1 $\mu$sec to about 500 msec), lasers are particularly suitable. For studying microscopic structures such as biological cell samples, a laser-scanning microscope is especially useful. Where the visual field contains approximately $10^5$ data points, a laser-scanning microscope capable of scanning the visual field in about 30 msec can scan a single point in the visual field in about one-third of a $\mu$sec. Preferred lasers include excimer lasers, tunable dye lasers, free-electron lasers, helium-neon and helium-cadmium lasers, and argon, xenon and krypton lasers. Optical equipment, such as suitable mirrors and suitable detectors, is chosen as needed to suitably meet the characteristics of the dye(s) chosen and the requirements of the laser selected.

As shown in FIG. 3, filter 2 may be of the wheel-type (filter wheel) or a plate-like multi-position changer (filter plate). The filter plate is equipped with arms fitted with filters which provide the desired wavelength of light. The arms alternate being positioned to intercept the excitation light beam, depending on the wavelength of light chosen. Grating monochromators are also suitable for providing the desired excitation wavelength.

The filter wheel is a disc provided with filters positioned near its circumference which provide the desired wavelength of light when positioned to intercept the excitation light beam. However, a filter plate having alternating arms equipped with interference filters, each of which provides a desired wavelength or range of wavelengths of excitation light when positioned to intercept the excitation light beam, is preferred.

Dichroic mirror 3 is selected such that the excitation light is reflected towards the sample, and the emission light passes through. Any conventional dichroic mirror known in the art which reflects excitation light and transmits emission light is suitable for use in the present invention. Suitable dichroic mirrors are commercially available from Oriel Corporation, Stratford, Connecticut, and Carl Zeiss, Thornwood, New York. However, preferred mirrors are those which, when used at a 45° incidence, reflect long wave ultraviolet and short wave visible light (from 360 to 440 nm) and transmit long wave visible and infrared light (>440 nm). A particularly preferred dichroic mirror is the ultraviolet reflecting mirror obtainable from Oriel Corporation, Stratford, Connecticut. For dual excitation/dual emission luminescence ratioing (monitoring of four independent emissions) and for monitoring combinations of fluoresceine and rhodamine (such as in the fluoresceine- and rhodamine-labelled enzyme F1CRhR, described below), a conventional multiple wavelength dichroic mirror is also suitable. A multiple wavelength dichroic mirror is available from Omega Optical, Brattleborough, New Hampshire.

After absorbance of the excitation light, the luminescent substance becomes electronically excited, then emits light of a longer wavelength. The distinction between fluorescence and phosphorescence is that fluorescence does not involve a change in the spin state of the electrically excited substance, whereas phosphorescence involves a change in the spin state of the excited substance (e.g., from the singlet state to the triplet state). Since the detection of fluorescence and phosphorescence involve measurement of emission light, the present process is applicable to both fluorescent and phosphorescent substances and processes.

The present method can be used to monitor the emission behavior of a single substance which exhibits dual emission phenomena, more than one fluorescent substance, one or more fluorescent substance and one or more luminescent substances, or one or more fluorescent substances and one or more autoluminescent substances. Suitable fluorescent dyes which exhibit different emission phenomena depending on their interaction with another substance include Fura-2, Indo-1, Fluo-3 (each of which is obtainable from Molecular Probes, Junction City, Oregon, and Sigma Chemical Co., Milwaukee, Wisconsin), fluorescein and its derivatives (e.g., carboxyfluorescein, fluorescein diacetate, carboxyfluorescein diacetate (CFDA), CFDA acetoxymethyl ester, 2',7'-bis-(carboxyethyl)-5(6)-carboxyfluorescein (BCECF), sulfofluorescein, sulfofluorescein diacetate, dichlorosulfofluorescein, dichlorsulfofluorescein diacetate, dimethylsulfofluorescein, dimethylsulfofluorescein diacetate), eosin, eosin diacetate, hydroxycoumarins H-189, H-185, H-1428 and their corresponding acetates, naphthofluorescein, carboxynaphthofluorescein and their corresponding diacetates, resorufin, resorufin acetate, dihydroxyphthalonitrile, SNARF-1, SNARF--2, SNARF--6 and SNARF-X (SNARF = seminaphthorhodafluor; trademark of Molecular Probes, Inc., Junction City, Oregon), SNAFL-1 and SNAFL-2 (SNAFL =seminaphthofluorescein; trademark of Molecular Probes, Inc., Junction City, Oregon), fluorescamine, rhodamine and its derivatives, etc. The SNARF and SNAFL reagents have the following structures:

SNARF-1
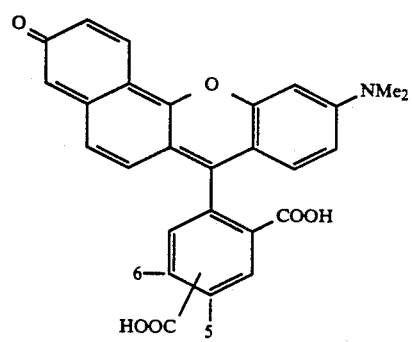

SNARF-2
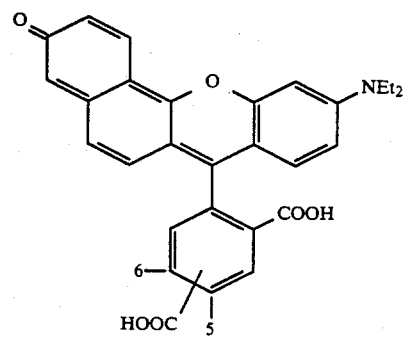

SNARF-6
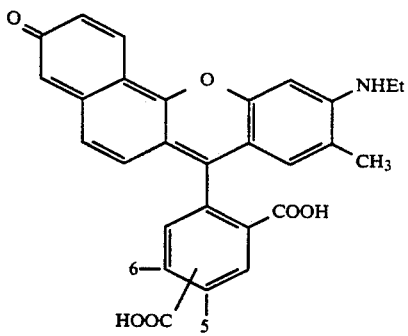

SNARF-X
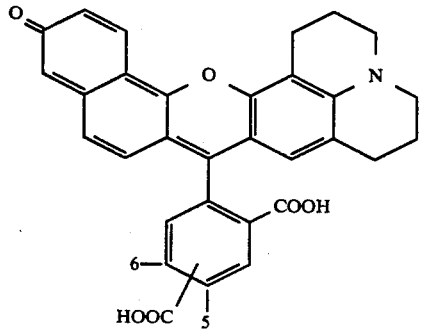

SNAFL-1
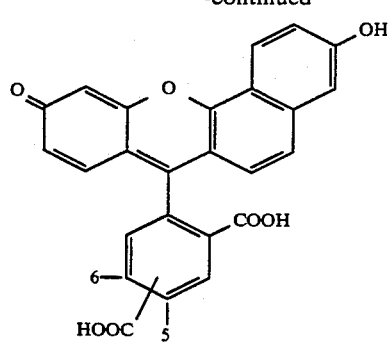

SNAFL-2
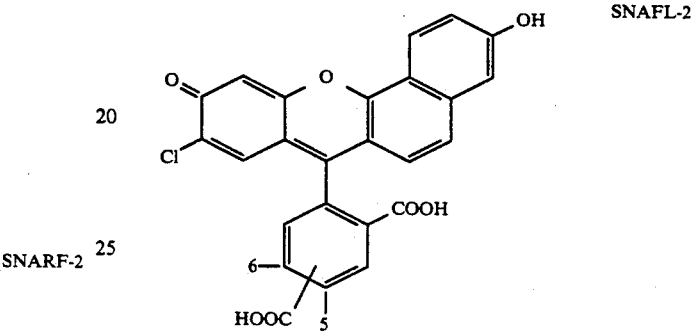

Autofluorescent substances include NADPH, cytochrome P-450, flavins (e.g., flavin adenine dinucleotide (FAD), flavin adenine mononucleotide (FMN), etc.

The fluorescent substances above display different emission phenomena, depending on the presence of another substance. Particularly notable substances affecting the emission behavior of the luminescent substances are metal ions, notably alkali metal ions (e.g., lithium, sodium, potassium, etc.), alkaline earth metal ions (e.g., magnesium, calcium, etc.), cyclic adenosine monophosphate (cAMP), and protons or hydroxide ions (pH-dependent luminescent behavior).

Figure 4:
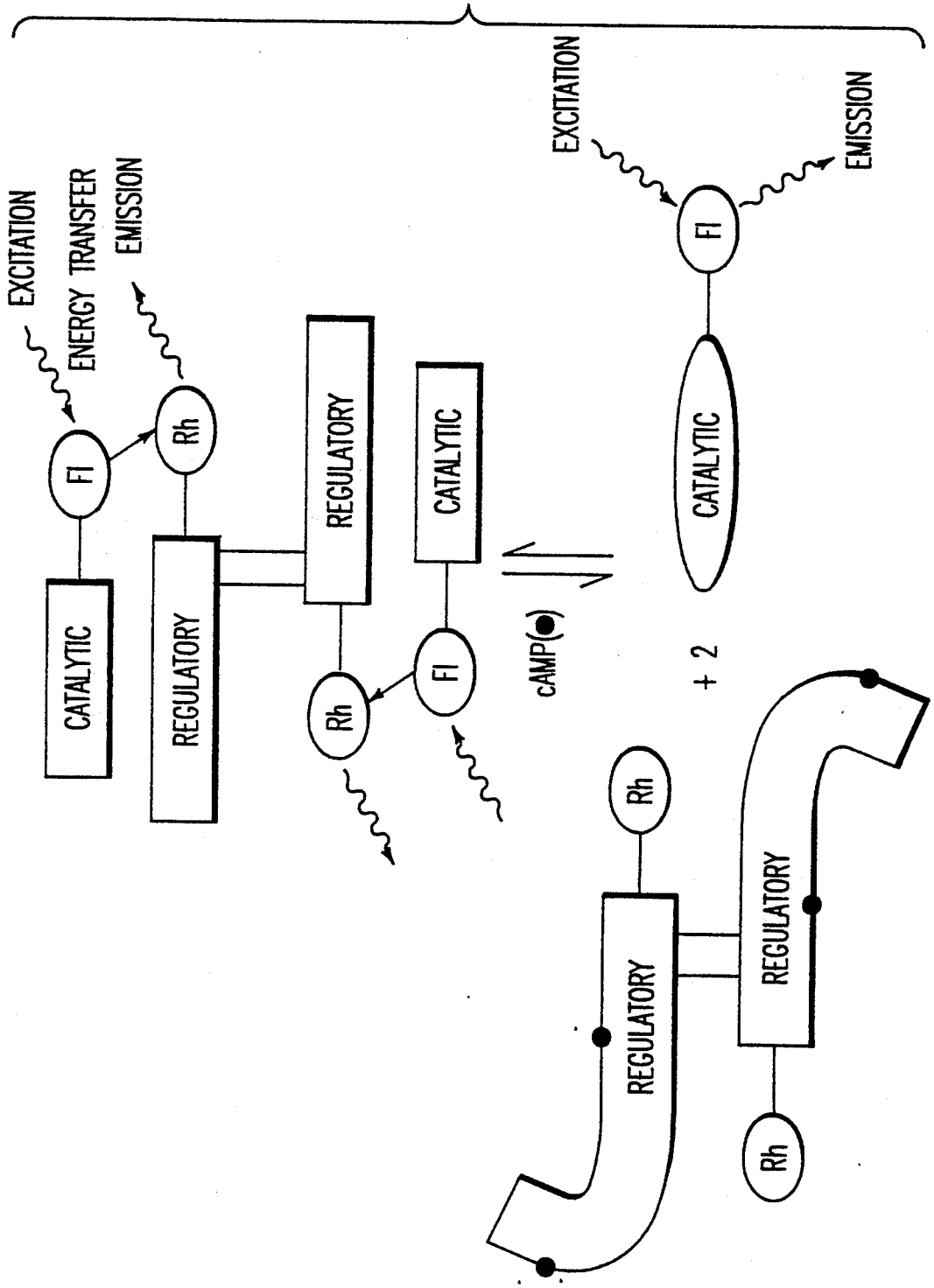
FIG. 4 is a chemical equation showing the relationship between cyclic adenosine monophosphate (cAMP) and a fluoresceine- and rhodamine-labelled cAMP-dependant protein kinase enzyme (F1CRhR)

The luminescent/fluorescent substance may be linked to another molecule or species. Furthermore, energy transfer between luminescent species may be studied. A suitable example of such a system is the cAMP-dependent protein kinase enzyme, to which both fluoresceine and rhodamine have been covalently linked. The cAMP-dependent protein kinase enzyme consists of four subunits, two catalytic and two regulatory ($C_2R_2$), as shown in FIG. 4. In the presence of high concentrations of cAMP, the catalytic subunits dissociate from the regulatory subunits. As a result, normal fluoresceine excitation/ emission behavior is observed in the presence of high concentrations of cAMP. On the other hand, in the absence of cAMP, the catalytic subunits are associated with the regulatory subunits. As a result, irradiation of F1CRhR with, for example, 480-495 nm light, which electronically excites fluoresceine and usually causes fluoresceine to fluoresce, actually results in energy transfer from the electronically excited fluoresceine to the ground state rhodamine, since the two fluorescent species are in such close proximity (see the top part of FIG. 4, which shows the associated F1CRhR complex). After energy transfer, rhodamine becomes electronically excited, and the electronically excited rhodamine emits fluorescence energy. By monitoring the relative fluorescence emission intensities of fluoresceine and rhodamine, one is able to determine concentrations of cAMP in a given biological cell sample. The relative fluorescence emission intensities of fluoresceine and rhodamine are easily monitored using ratio imaging techniques.

The luminescence-affecting chemical species affect the fluorescence of the fluorescent compounds. Particularly notable relationships between fluorescence-affecting chemical species and the fluorescent emissions of one of the fluorescent substances include the following: (a) Fura-2 and $Ca^{2+}$; (b) Indo-1 and $Ca^{2+}$; (c) Indo-1 and $Mg^{2+}$; (d) fluo-3 and $Ca^{2+}$; (e) fluorescein (and its derivatives) and pH; (f) the SNARF reagents and pH; (g) BCECF and pH; (h) cAMP and FlCRhR, which is a dual emission/single excitation system (the cAMP/F1CRhR system is excited at 488 nm, and emissions are monitored at 520 nm and 580 run); and (i) fluorescamine and primary amines.

Where the concentrations of at least two luminescence-affecting chemical species are of interest, particularly notable combinations of luminescence-affecting chemical species (and particularly fluorescence-affecting chemical species) include (i) pH and $Ca^{2+}$, (ii) cAMP and $Ca^{2+}$, and (iii) cAMP, $Ca^{2+}$ and propidium iodide. The preferred corresponding fluorescent compounds in combination with the luminescence-affecting chemical species (i), (ii) and (iii) above include (I) pH and BCECF, and $Ca^{2+}$ and fura-2; (II) cAMP and FlCRhR, and $Ca^{2+}$ and fura-2; and (III) cAMP and FlCRhR, $Ca^{2+}$ and indo-1, and propidium iodide, which displays different fluorescence behavior depending on its intercalation into the DNA or RNA of a cell. Propidium iodide cannot intercalate into the polynucleic acid of a cell until the cell dies and the cell membrane becomes permeable to the charged propidium iodide. Thus, propidium iodide acts as an indicator of cell viability.

Phosphorescence ratios can be determined in a manner analogous to the techniques discussed herein for fluorescence ratios. Corresponding phosphorescence ratio images can be produced using analogous equipment to that described herein for producing fluorescence ratio images.

Suitable phosphorescent substrates include, for example, semiconductors and phosphors (e.g., zinc sulfide, zinc oxide, cadmium sulfide, the phosphorescent behavior of which changes depending upon dopants and the strength of an applied electromagnetic field. Ceramic materials are also suitable phosphorescent substrates, as are light-emitting diodes (e.g., GaP, which may be doped with Zn, GaAs, which may be doped with Zn or Si, $GaP_xAs_{1-x}$, AlGaAsInP, GaInPAs, each of which may be doped with Zn or Te, ZnO, N). Phosphors include calcium and/or strontium halophosphates which may be doped with antimony (Sb), manganese (Mn), mixtures of Sb and Mn, europium (II) (Eu), yttrium oxide, vanadate or phosphate vanadate, doped with Eu(II) or Eu(III); barium magnesium aluminate or cerium magnesium terbium aluminate. Copper(II) is also a useful dopant. Ions such as $VO_4^{3-}$, $(WO_6)^{6-}$, $(UO_2)^+$ and $(UO_6)^{6-}$ are suitable phosphorescent substances, as are most transition metal ions, such as Mn(IV), Fe(III) and Cr(III), in addition to those already mentioned.

The advantage to the present method with regard to phosphorescent materials lies in the detection of particular substances in particular regions of a given matrix of the material without having to realign the sample field.

Detector 6 comprises a camera having a photosensitive element and a means for augmenting the electrical signals produced in the photosensitive element. A conventional intensified charge-couple device (CCD), known to those in the art, is suitable for use as the detector 6. However, a preferred camera which includes the preferred photosensitive element and means for augmenting the electrical signals is that accompanying the ATTOFLUOR TM Digital Fluorescence Microscopy System (Trademark, Atto Instruments, Rockville, Maryland).

Figure 5:
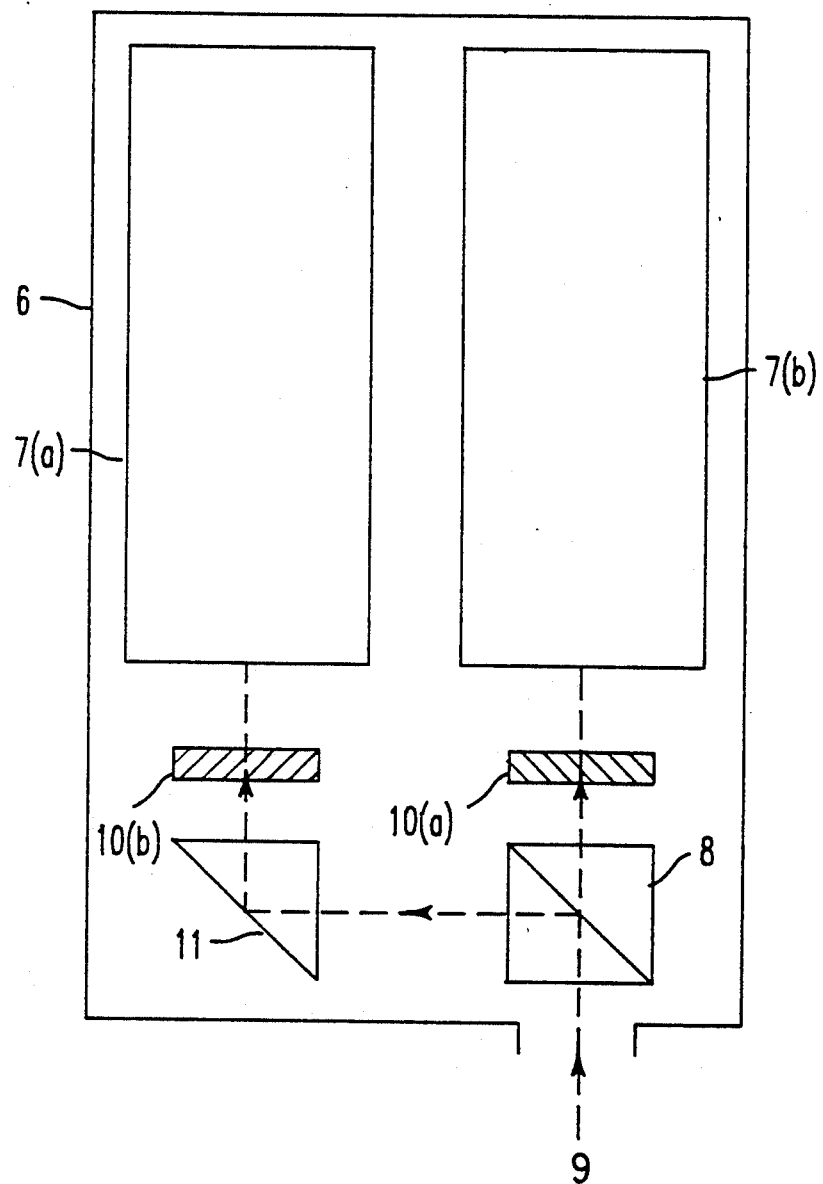
FIG. 5 shows a two-camera detector.

Optionally, as shown in FIG. 5, detector 6 can be fitted with two cameras 7(a) and 7(b) A conventional beam-splitter 8 is used to separate the reflected emission beam 9 into component wavelength ranges, prior to interception of the emission beam by the filters 10(a) and 10(b). Filters 10(a) and 10(b) are made of one or more suitable, conventional wavelength-selective materials, which are generally known in the art. The emission beam wavelength range reflected to camera 7(a) by is beam-splitter 8 is directed towards filter 10(a) by a prism or mirror 11. The two-camera system provides an advantage in the precise simultaneous monitoring of two separate, independent emissions. However, the disadvantage of the two-camera system is that the photosensors must be exactly aligned to provide reliable results.

An optional device for the apparatus is a filter wheel, positioned in front of the detector, to aid or enhance the ability of the detector to detect selected wavelengths of emission light.

Figure 6:
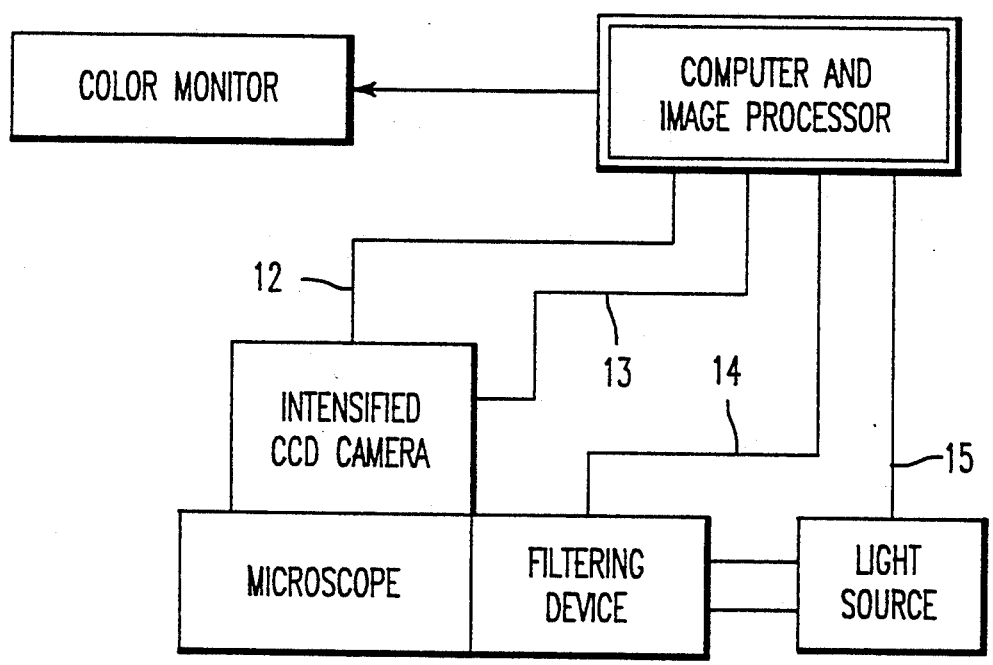
FIG. 6 is a schematic diagram of a suitable instrument for conducting the present multiple emission ratioing method, including an appropriate control system.

One key to the present invention is the ability to precisely measure four independent emission phenomena within a period of time of from about one microsecond to one minute, preferably from one millisecond to 30 seconds, most preferably from 50 milliseconds to 10 seconds. This ability is achieved by an electronic switching device, which either (a) precisely changes the gain setting on the photosensitive element simultaneously with changes in excitation wavelength employed and/or emission wavelength detected, thus automatically adjusting the sensitivity of the detector, or (b) precisely changes the intensity of the excitation light source simultaneously with changes in the emission event being detected, to detect any and all emission events within the optimal dynamic range of the photosensitive element. A suitable instrument for conducting the present method, including a control system, is depicted schematically in FIG. 6. Each of lines 12-15 respectively represent a gain control line (12), inputting data from the computer and image processor to the camera, a video input line (13), feeding image data from the camera to the computer and image processor, a control line (14) between the computer and the light filtering device to permit the computer to regulate switching of the filters, and an intensity control line (15) between the computer and the light source to permit the computer to regulate the intensity of the excitation light.

A suitable gain control for precisely changing the gain setting on the photosensitive element simultaneously with changes in excitation wavelength employed and/or emission wavelength detected can be found in the ATTOFLUOR TM Digital Microscopy System, sold by Atto Instruments, Inc., Rockville, Maryland.

Alternatively, the intensity of the excitation light can be varied to provide the desired emission intensities within the optimal dynamic range of the photosensitive element. A means for switching of the wavelengths and intensities of excitation energy can be provided by a computer equipped with appropriate hardware and software, accompanied by appropriate circuitry to precisely control the switching to the appropriate wavelengths and intensity levels. However, the preferred method of controlling emissions so that they are monitored within the optimal dynamic range of the photosensitive element is the switching device which changes the gain setting on the photosensitive element, particularly that found in the ATTOFLUOR ™ Digital Microscopy System.

The preferred control system is a computer equipped with hardware and software provided for the ATTOFLUOR ™ Digital Microscopy System, sold by Atto Instruments, Inc., Rockville, Maryland.

Samples are prepared and mounted by conventional methods, known to those in the art. Typically, samples are prepared and mounted under ambient conditions (a temperature of 15°–40° C., atmospheric pressure, in air). However, some samples may require special preparation or irradiation conditions. For example, air-sensitive semiconductor samples and materials or anaerobic cell samples may require preparation under an inert atmosphere, as might samples which contain luminescent species subject to rapid quenching by oxygen or other air-borne luminescence quenchers; gas-phase samples may require preparation under high pressure or under vacuum; intensities of short-lived luminescent phenomena may require measurement at low temperatures, etc. The present invention is not limited to ambient temperatures, pressures and atmospheres, and is intended to encompass other conditions. For example, an upright microscope may be employed for monitoring luminescence phenomena of samples requiring mounting on such an instrument. Furthermore, the instrument can be used and/or can be equipped to be used under non-ambient conditions, such as in an inert atmosphere box or inert atmosphere room, a "clean" room such as is used in processing of electrical devices and semiconductors, a cold room, etc.

The upper limit to the number of ratios which can be determined depends, in part, on the band width of the radiation spectrum available to conduct photoluminescence measurements, and at least in part, on the number of distinct bands of wavelengths of luminescent emissions which can be produced and detected. The resolution of light filters to produce narrow bands of excitation light and of the photodetectors to detect narrow bands of emission light limit resolution of the process to bandwidths of about 2–10 nm. In this respect, for example, excitation or detection of light at 334 nm is equivalent to excitation or detection at 340 nm.

Figure 7A:
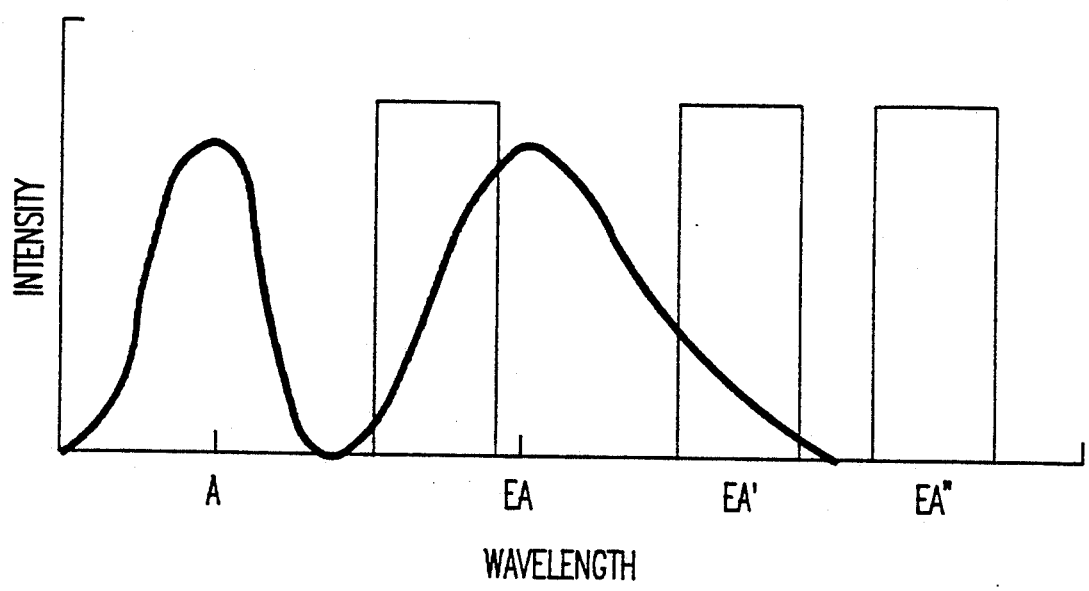
FIGS. 7A and 7B show the hypothetical luminescence behavior of two dyes, wherein the emission wavelengths being monitored overlap.
Figure 7B:
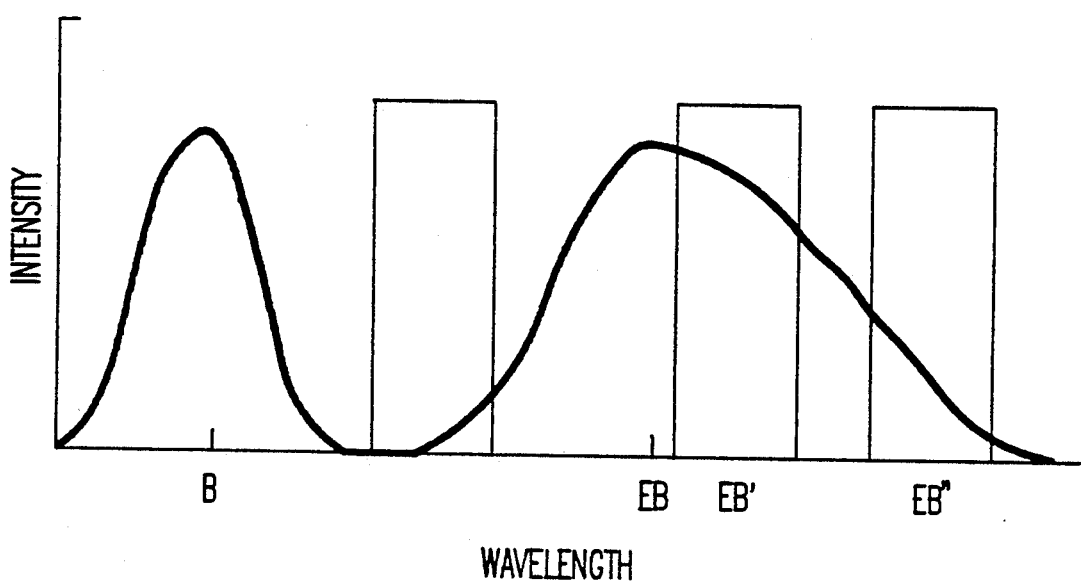

It is possible to get reliable results even if the emissions of two dyes are detected at the same wavelength, provided there is a difference in the emissions of the dyes at a wavelength other than those being monitored for the purposes of ratioing. For example, FIG. 7 shows the hypothetical luminescence behavior of two dyes, where A and B represent wavelength bands at which each of the dyes are excited, and EA and EB represent wavelength bands at which each of the dyes emit luminescent energy. By monitoring the emission intensity at the wavelength band corresponding to EB″ (at which only the dye corresponding to EB emits luminescence), one can determine the concentration of the dye or its complex with a luminescence-affecting species corresponding to EB″. This information can then be used to determine the emission intensities of this dye or its complex at wavelength band EB′. In turn, the relative proportion of EB′ emissions to the total emissions at that wavelength band can then be determined empirically. Thereafter, the intensity at the wavelength band corresponding to EA′ and EB′ is measured, and the relative proportion of EA′ emissions is calculated, leading to the determination of the concentration of the dye or complex corresponding to EA emissions.

Alternatively, the apparatus may comprise a Zeiss Upright AXIOSKOP (Trademark, manufactured by Carl Zeiss, Thornwood, New York) or a Zeiss AXIOVERT (Trademark, manufactured by Carl Zeiss, Thornwood, New York).

Other features of the invention will become apparent in the course of the following descriptions of exemplary embodiments which are given for illustrative of the invention, and are not intended to be limiting thereof.

EXAMPLES

I. Fura-2 Calibration (1) Calibration Standards

Two standard solutions (standards) containing components in known concentrations were prepared for system calibration:

(a) Fura-2; and (b) Fura-2 + $Ca^{2+}$.

The concentration of Fura-2 in the standard solutions was from 10 $\mu$M to 25 $\mu$M. The concentration of the standards depended upon the brightness and expected specimen loading concentrations of the samples tested. Brighter test samples required calibrating the instrument with standard solutions of higher Fura-2 concentration.

Using a black marker, a line to aid focusing was drawn on the bottom of the calibration sample holder (coverslip), and the line was allowed to dry. A "+" was marked on one side of the line and a "−" on the other.

Figure 8A:
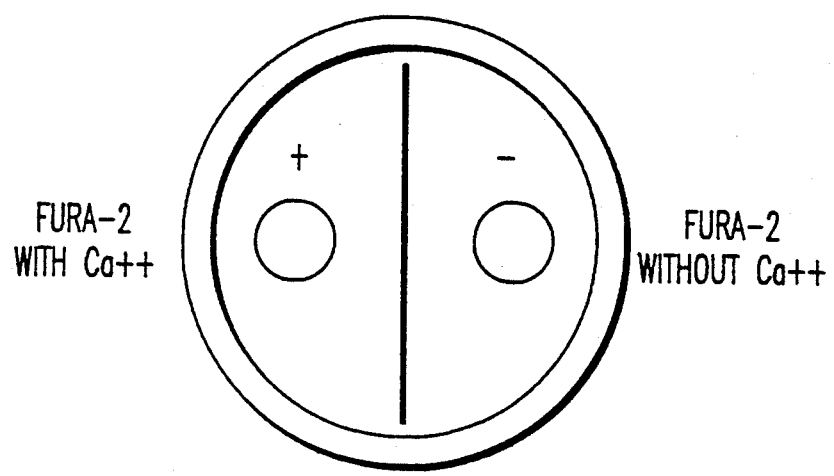
FIGS. 8A and 8B show a top view of a standard calibration sample.
Figure 8B:
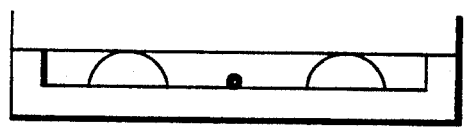

Standard calibration samples were prepared by pipetting 5 $\mu$l of the standard solution containing $Ca^{2+}$ onto the "+" side of the drawn line, pipetting 5 $\mu$l of the standard solution not containing $Ca^{2+}$ onto the "−" side of the drawn line, and covering with a coverslip. A standard calibration sample is shown diagrammatically in FIG. 8.

(2) Calibrating the Fluorescence Detector

Fluorescence imaging was conducted with an ATTOFLUOR ™ Digital Fluorescence Microscopy System (Atto Instruments, Rockville, Maryland)- The system consisted of a Zeiss AXIOVERT inverted epifluorescence microscope with all quartz optics. A 100 W mercury burner served as the excitation light source. For fura-2, excitation at either of two wavelength pairs was conducted: (i) at 340 nm and 380 nm, or (ii) at 334 nm and 390 nm. Bandpass interference filters (10 nm) providing the desired wavelength were alternately selected by a computer-controlled excitation and shutter control unit. Zeiss dichromatic beam splitters were used. Emissions were monitored with an intensified CCD camera the sensitivity of which was set independently for each wavelength, and then switched to that sensitivity by the computer just before each wavelength of excitation was selected. A 510-rim long-pass emission filter was used to select for emission fluorescence greater than 500 rum. The video signals were digitized to 8-bit resolution (256 shades of gray; 512×512 pixels per frame) in real time, and in most cases images were captured after a 30-msec shutter opening of the excitation source and one 30-msec video frame. In some cases five video frames were averaged. In addition to automatic capture and disk storage of the 340-nm and 380-nm ratioed images, the system also continuously calculated and graphically displayed the mean intensity of a 64-pixel box area (or larger) of the image. The outline of the box can be seen on the images. A data file of the pixel intensities and $Ca^{2+}$ concentration was saved by the computer. The samples were viewed through no. 1 glass coverslip dishes or glass six-well slides. A Zeiss 63 power Neofluor (numerical aperture, 1.3) objective was used.

Calibration provides background subtraction and correlation to $Ca^{2+}$ standards in real time, such that $Ca^{2+}$ concentration within the selected box area was displayed in graphical form versus time (calculated according to the procedure of Connor, J. A. *Proc. Natl. Acad. Sci. USA*, vol. 83 (1986), pp. 6179–6183).

The ATTOFLUOR ™ Digital Fluorescence Microscopy System (Atto Instruments, Rockville, Maryland) was set up and focused on the line according to the procedure provided with the instrument. The "−" standard was placed in the microscope field. The excitation wavelength was set to 380 nm. An even intensity region near the center of the field was identified and measured. The camera gain was adjusted until the field was bright but below maximum, adjusting the neutral density filter and/or objective diaphragm as needed.

The excitation wavelength was changed to 340 nm. The intensity was lowered via the intensity gain until the field was dim but above minimum, adjusting the neutral density filter and/or objective diaphragm as needed. Adjustment of the intensity at 380 nm was repeated, then adjustment of the intensity at 340 nm, until acceptably contrasting results (gray values) were obtained for both excitation wavelengths. By this procedure, the instrument was calibrated to a sample containing fura-2 but no $Ca^{2+}$.

The "+" standard was placed in the microscope field, and the excitation wavelength was set to 340 nm. The intensity was adjusted until the field was bright but below maximum, adjusting the neutral density filter and/or objective diaphragm, if needed. The excitation wavelength was changed to 380 nm, and the intensity was adjusted until the field was dim but above minimum, adjusting the neutral density filter and/or objective diaphragm, if needed. Adjustment of the intensity at 340 nm was repeated, then adjustment of the intensity at 380 nm, until acceptably contrasting results (gray values) were obtained for both excitation wavelengths. By this procedure, the instrument was calibrated to a sample containing both fura-2 and $Ca^{2+}$.

The "−" standard was placed in the microscope field. The camera gain was fine-tuned (if required) to insure that the intensity values for the "−" standard at both excitation wavelengths are in the dynamic range of the camera. Fine-tuning of the camera gain was repeated for the "+" standard. Fine-tuning was then repeated until acceptable values were obtained for both standards at both excitation wavelengths with a single camera gain set-up (see Table 1 below).

TABLE I

| Fura-2 Only | | Fura-2 + $Ca^{2+}$ | |
|---|---|---|---|
| Excitation Wavelength | Intensity (Gray Value) | Excitation Wavelength | Intensity (Gray Value) |

TABLE I-continued

| | | | |
|---|---|---|---|
| 340 nm | 20–50 | 340 nm | 180–240 |
| 380 nm | 180–240 | 380 nm | 20–50 |

The calibration values are entered into the computer. Measurements on both the "+" and "−" standards are taken over the course of several minutes to an hour. Values representative of the measurements taken for the "−" standard serve as values for "380(Lo)" and "R(Lo)" in Equation (I) above, and values representative of the measurements taken for the "+" standard serve as values for "380(Hi)" and "R(Hi)" in Equation (I) above. Using the ATTOFLUOR ™ Digital Fluorescence Microscopy System, the results are printed out as follows:

EXAMPLE SHEET:
    Wed Oct 24 12:15:53 1990

ATTOFLUOR DIGITAL MICROSCOPY
    (c) 1989 Atto Instruments, Inc.
33 208 250  79 145 0.546  Notation: Lo *Ca++
                                      (Fura-2 only)
39 226 320 161  49 3.265  Notation: Hi *Ca++
                                      (Fura-2 + $Ca^{2+}$)
1  2  3  4  5  6  < (COLUMN NUMBER)
                  └─ ratio
              └─ grey value at 380 nm
          └─ grey value at 340 nm
        └─ milliseconds
     └─ seconds (from last reset)
└─ sample number

| | R(Lo) = 0.546 |
|---|---|
| RESULTING | R(Hi) = 3.265 |
| CALIBRATION VALUES | 380(Lo) = 145 |
| | 380(Hi) = 49 |

The calibration values were entered into the computer, and the calibration curve appeared on the monitor, thereby calibrating the system for fura-2.

In general, calibration insures that all intensity values obtained during an experiment fall within the dynamic range of the detector, since the detector is calibrated using maximum and minimum standards.

II. Calibration of Other Systems

Unless otherwise specified, the calibration procedure above for fura-2 was repeated for each of the following systems, making changes in irradiation or detection wavelengths as needed.

(A) Fluo-3/$Ca^{2+}$

Fluo-3 is a single excitation/single emission dye. A 485-nm interference filter with a 20-nm bandpass was substituted for the dual 340 nm/380 nm filters to provide the desired excitation light. Fluo-3 emission was monitored at >500 nm.

(B) Indo-1/$Ca^{2+}$

Indo-1 is a single excitation/dual emission dye. Indo-1 was excited with either 340 or 360 nm light, and its emissions at 460 nm and 520 nm were monitored. Either 340 or 360 nm light can be used to effectively excite indo-1.

(C) BCECF/pH

BCECF is a dual excitation/single emission dye. BCECF was excited with 460 nm and 488 nm light, and its emissions at >510 nm were monitored.

(D) F1CRhR/cAMP

F1CRhR is a single excitation/dual emission dye system (as described above). F1CRhR was excited with 488 nm light, and its emissions at 520 nm and 580 nm were monitored. The use and monitoring of fluorescence ratios with F1CRhR to determine cAMP concentration is detailed in Adams et al, *Nature*, vol. 349 <1991), pp. 694–697.

Figure 9:
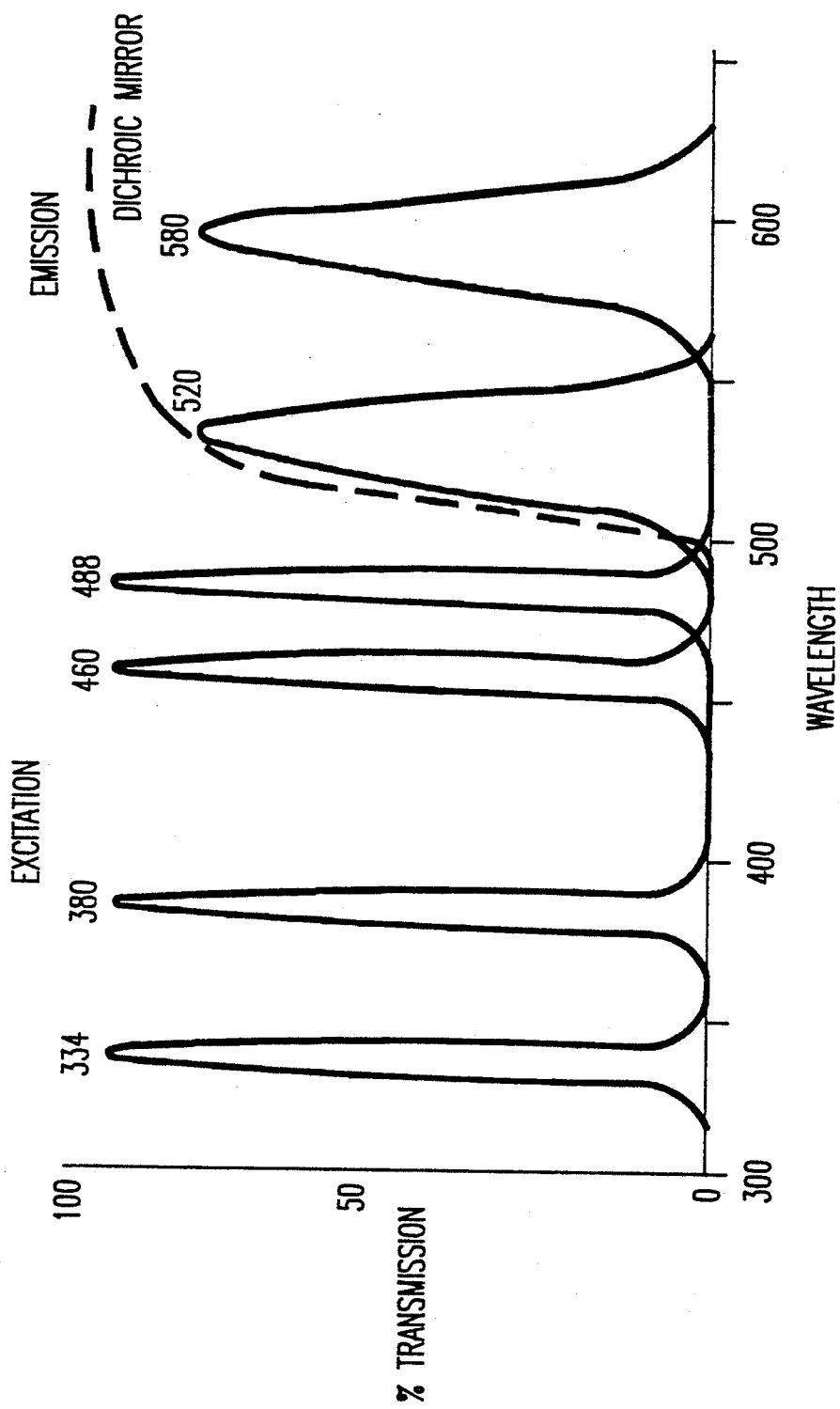
FIG. 9 shows the theoretical fluorescence characteristics of two dual excitation/single emission fluorescent dyes and the single excitation/dual emission F1CRhR dye-labelled protein.

FIG. 9 shows the theoretical fluorescence characteristics of two dual excitation/single emission fluorescent dyes and the single excitation/dual emission F1CRhR dye-labelled protein. In FIG. 9, the % transmission peaks at 334 and 380 nm represent absorption of excitation light by fura-2. The % transmission peaks at 460 and 488 nm represent absorption of excitation light by BCECF. The peak at 488 nm also represents absorption of excitation light by F1CRhR. On the other hand, the peak at 520 nm represents the emission of fluorescence energy by fura-2 and BCECF, and both of the peaks at 520 and 580 nm represent the emissions of fluorescence energy by F1CRhR.

EXAMPLE 1

The experiment of Example 1 simultaneously monitored the relationship between fura-2 fluorescence to measure calcium ion concentration and BCECF fluorescence to measure pH (two dual excitation/single emission ratios were determined). Monolayer cultures of C6-2B rat astrocytoma cells (passage 10–30) were grown at 37° C. in Ham's F-10 nutrient medium buffered with 14 mM $NaHCO_3$ (pH 7.4), supplemented with 10% donor calf serum, in six-well plates having a 25 mm glass coverslip placed on the bottom of each dish, in a humidified atmosphere of 5% $CO_2$/95% air. The cells were plated with 2 ml of media at $5 \times 10^3$ cells per well After seven days the medium is removed, and 1 ml of new medium is added. On the eighth day, the cells were confluent with a protein content of about 150 μg protein/well. Microscopic multiple fluorescence ratio imaging of the cells was performed using an ATTOFLUOR Digital Fluorescence Microscopy system, based on a Zeiss AXIOVERT microscope. Cells were loaded with Fura-2 AM (5 μm) and BCECF (0.1 μm) for 30 min, and the loaded cells were washed for 10 min with a suitable buffer. Fura-2 was irradiated at 334 and 380 nm, and BCECF was irradiated at 460 and 488 nm. Intensities of all emissions were measured at wavelengths above 525 nm.

Figure 10A:
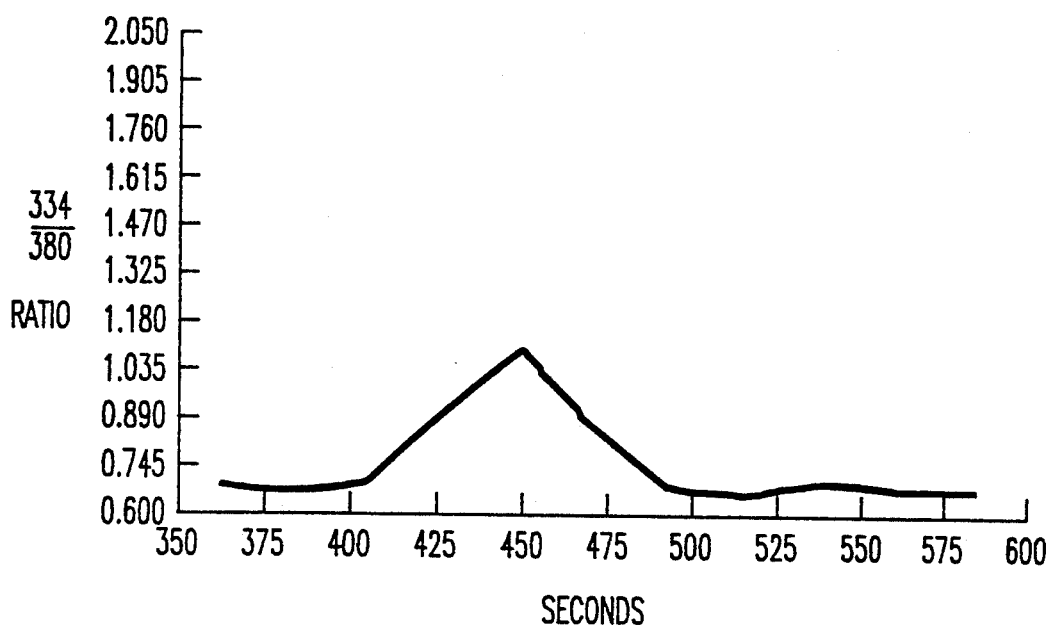
FIGS. 10(A) and 10(B) show the changes in $Ca^{2+}$-concentration (fura-2 emission ratio) and fura-2 emission intensities, respectively, for a given location in a cell with respect to time.
Figure 10B:
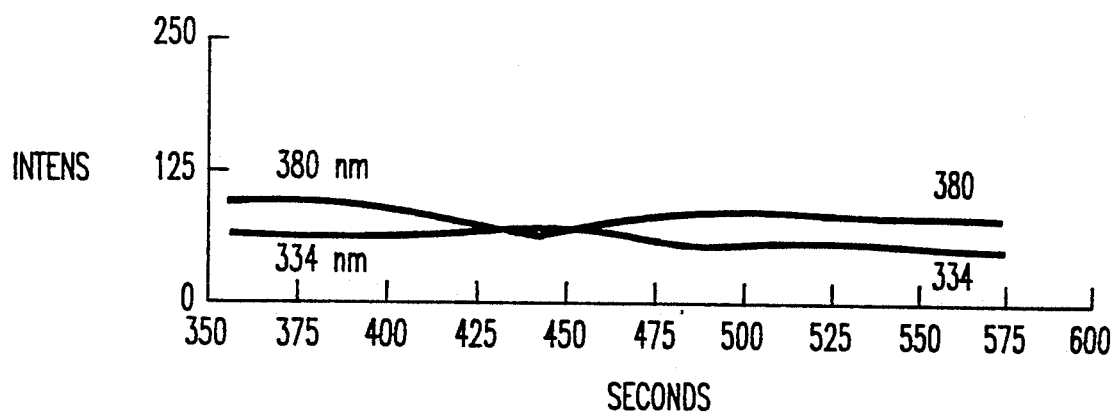
Figure 11A:
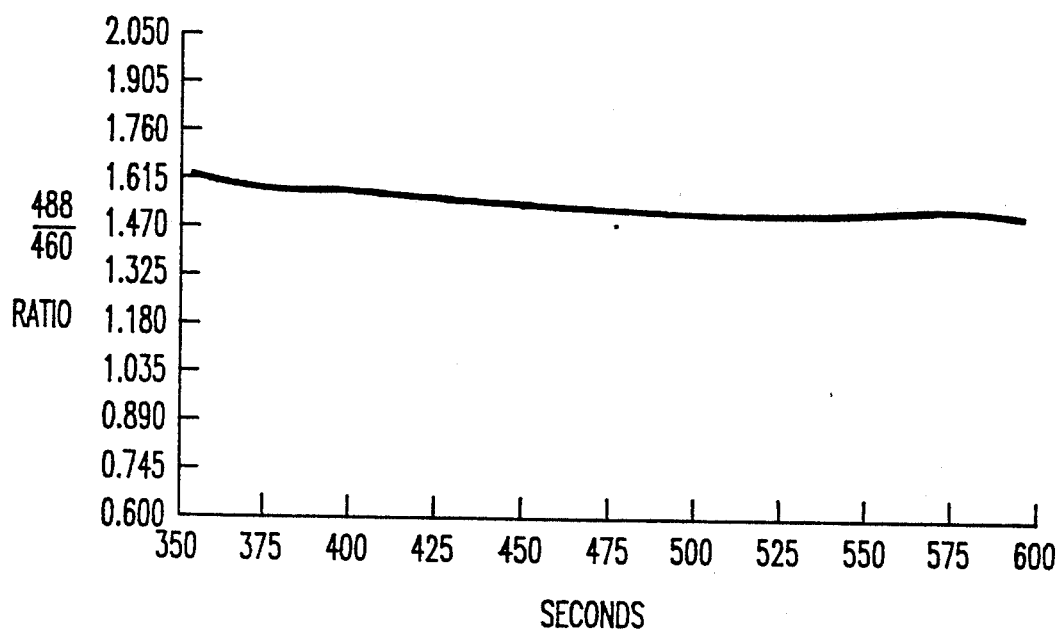
FIGS. 11(A) and 11(B) show the changes in pH (BCECF emission ratio) and BCECF emission intensities, respectively, for the same location in the same cell as FIGS. 10(A) and 10(B) with respect to time.
Figure 11B:
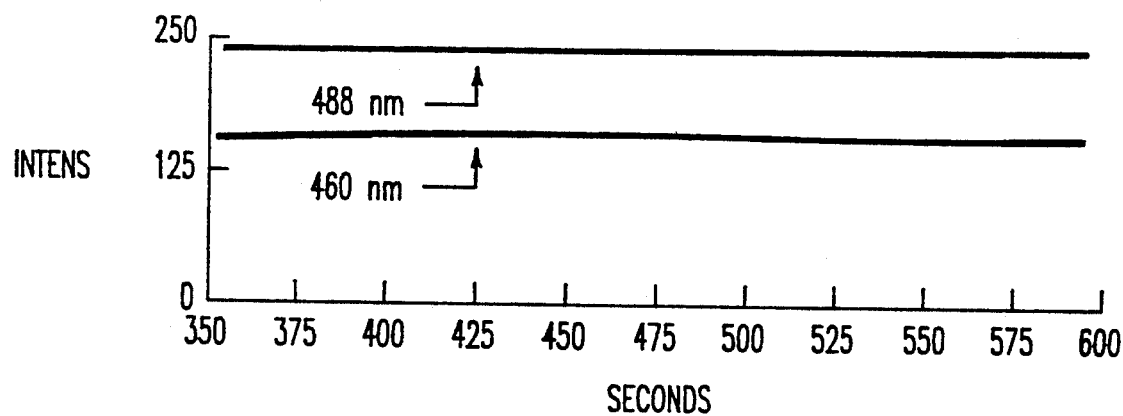

FIG. 10(A) shows the changes in the 334 nm/380 nm fura-2 emission ratio, which is proportional to $Ca^{2+}$ concentration, for a given location in a cell with respect to time after addition of 1 μM substance K. FIG. 10(B) shows the raw intensity data of fura-2 emission intensities at 525 nm, when excited first at 334 nm, then at 380 nm, for the same given location in the cell. FIG. 11(A) shows the changes in the 488 nm/460 nm BCECF emission ratio, which is proportional to the pH at a given location in a cell with respect to time after addition of 1 μM substance K. FIG. 11(B) shows the raw intensity data of BCECF emission intensities at 525 nm, when excited first at 460 nm, then at 488 nm, for the same given location in the cell.

specifically, the single peak observed at about 450 seconds in FIG. 10(A) reveals an abrupt change in $Ca^{2+}$ concentration, whereas FIGS. 11(A) and 11(B) show no corresponding change in pH in response to substance K.

Figure 12A:
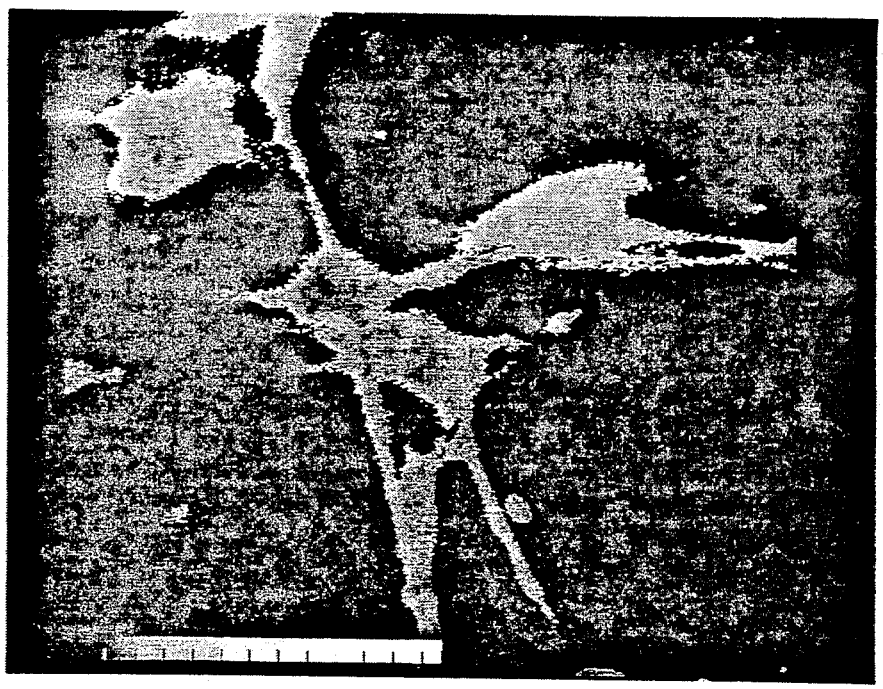
FIGS. 12(A) and 12(B) show fluorescence ratio images of $Ca^{2+}$ concentration and pH, respectively, in the cells in the experiment of Example 1.
Figure 12B:

FIG. 12(A) shows a fluorescence ratio image of $Ca^{2+}$ concentration of the entire visual field in this experiment. FIG. 12(B) shows a fluorescence ratio image of pH concentration of the entire visual field in this experiment. About eight or nine cells are shown.

EXAMPLE 2

The relationships between fura-2 fluorescence to measure calcium ion concentration and F1CRhR fluorescence to measure cAMP concentration can be simultaneously monitored (one dual excitation/single emission ratio and one single excitation/dual emission ratio). In this system, fura-2 is irradiated at 334 and 380 nm, and the emission intensities are measured at wavelengths above 520 nm by use of a 520 nm bandpass filter. F1CRhR is irradiated at 488 nm, and monitored at 520 nm and 580 nm.

EXAMPLE 3

The relationships between indo-1 fluorescence to measure calcium ion concentration and F1CRhR fluorescence to measure cAMP concentration can be simultaneously monitored (two single excitation/dual emission ratios were determined). conventional microinjection equipment and techniques for microinjection of dyes and test substances into cells is employed to inject the fluorescent compounds into the cells.

EXAMPLE 4

The experiment of Example 4 simultaneously monitors the relationships between fura-2 fluorescence to measure calcium ion concentration, F1CRhR fluorescence to measure cAMP concentration and propidium iodide fluorescence to determine cell viability (one dual excitation/single emission ratio, one single excitation/dual emission ratio and one qualitative fluorescence were determined). The concentration of cAMP using F1CRhR is monitored as described above and/or as described by Adams et al, *Nature*, vol 349, pp 694–697 (1991). Fura-2 fluorescence to measure calcium ion concentration is performed as described above. Propidium iodide is excited at 334 nm, and fluorescence is monitored at $\geq 640$ nm.

COMPARATIVE EXAMPLE

In this experiment, the relationships between fura-2 fluorescence to measure calcium ion concentration and propidium iodide fluorescence to measure cell viability were evaluated using the ATTOFLUOR ™ Digital Fluorescence Microscopy system (Atto Instruments, Rockville, Maryland), with adjustments made to monitor a single ratio.

Seven- to eight-day-old primary cultures of rat cerebellar granule cells were prepared from eight-day-old Sprague-Dawley rats (Zibic-Miller, Pittsburgh, Pennsylvania). Neurons were grown in 35-mm culture dishes containing 25-mm glass cover slips (obtained from Fischer Scientific Co., No. 1) coated with poly(L-lysine). Glial proliferation was prevented by adding cytosine arabinonucleoside (final concentration =10 μM) 24 h after plating. Immunocytochemical studies of primary cultures of the cerebral or granule cells show that they contained greater than 95% neurons and less than 5% glia or other contaminating cells (Vaccarino et al, *J. Neurosci.*, 7:65–76). Calcium ion imaging data were derived only from neurons.

The cells grown on glass coverslips were loaded with 5 μM fura-2 acetoxymethyl ester for 30 min in Locke's buffer (154 mM NaCl/5.6 mM KCl/3.6 mM $NaHCO_3$/2.3 mM $CaCl_2$/1.2 mM $MgCl_2$/5.6 mM glucose/5 mM Hepes, pH 7.4) at 37° C. and then mounted in a 35-mm holder that created a chamber with the coverslip on the bottom, according to the method of Ince et al, *Pflugers Arch.*, 403:240-244 (1985). After loading with fura-2 but before the beginning of the experiments, the cells were given 5-10 min to allow fura-2 deesterification and equilibration between the bound and free forms. In experiments with propidium iodide, 0.7 $\mu$M propidium iodide was added to the perfusion fluid and was present at all times during the experiment. Both fura-2 and propidium iodide were excited at the wavelength pair of 334 nm and 390 nm by using 10-nm band-pass interference filters, which were alternately selected by the computer-controlled excitation and shutter control unit. The calcium ion concentration was measured by the ratio of fura-2 fluorescence excited by 334 nm to that excited by 390 nm and calibrated according to external standards, according to the methods of Brooker et al, *Proc. Natl. Acad. Sci. USA*, 87:2813-2817 (1990), and Connor, *Proc. Natl. Acad. Sci. USA*, 83:6179-6183 (1986). A Zeiss dichromatic beam splitter (FT 395) was used to separate the excitation beam from the emission image. A 510-nm long-pass emission filter was used to select fluorescence emission above 500 nm when only fura-2 was imaged. For simultaneous fura-2 and propidium iodide imaging, a combination emission filter set was used for fura-2 imaging. This combination emission filter prevents propidium iodide emission interference with the fura-2 image. To measure the red propidium iodide fluorescence free of interference from the fura-2 emission, the emission filter was manually switched to a red emission wavelength filter that excluded emission below 640 nm. The video signals were digitized to 8-bit resolution as described above for fura-2 calibration. In addition to automatic capture and disk storage of the 334-nm and 390-nm image pairs and/or ratioed images, the system also continuously calculated and graphically displayed the mean intensity of a variable-size pixel box area located on one of the cells in the field of view. For fura-2 images, the instrument was operated in the calibrated mode, in which background subtraction and correlation to $Ca^{2+}$ standards were performed in real time, such that $Ca^{2+}$ concentration within the selected box area was displayed in graphical form versus time by the procedure of Connor, *Proc. Natl. Acad. Sci. USA*, 83:6179-6183 (1986). For propidium iodide, images were taken every 5 min at 334 nm with background subtraction. For statistical calculations of propidium iodide data, the average pixel intensity (at 334-nm excitation) of a 96-pixel box area was considered. A data file of the pixel intensities for both dyes and $Ca^{2+}$ concentration $[Ca^{2+}]$ was saved by the computer.

Drugs, dissolved in Locke's solution, were perfused over the cells at 1 ml/min with a peristaltic pump while the cells were being imaged. $MgCl_2$ was routinely omitted from the solution during the exposure to glutamate (5-20 min, 22° C.). The volume in the dish was 500 $\mu$l. Thereafter, the cultures were washed three times with Locke's solution and then set in the perfusion system. Experiments were performed at room temperature ($\approx$22° C.).

Figure 13:
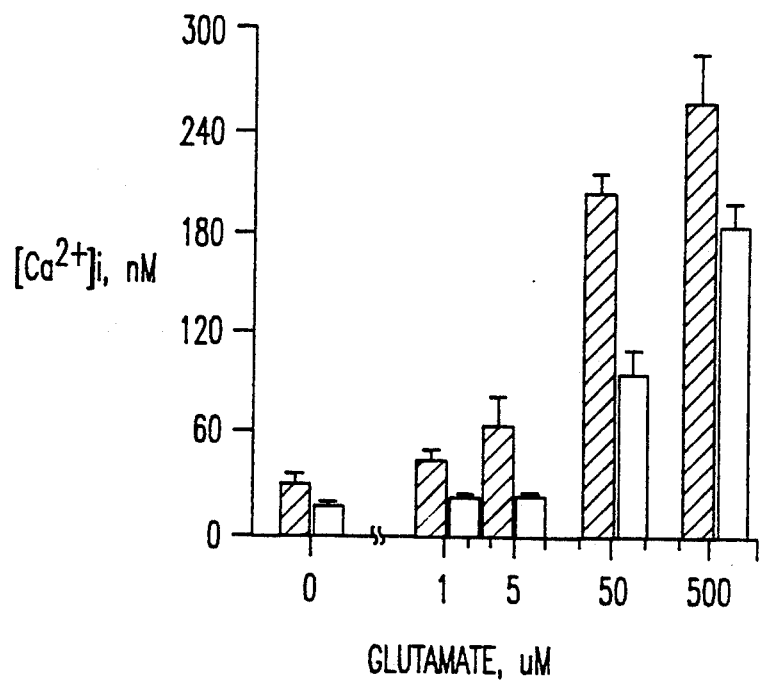
FIGS. 13 and 14 show the dose and time dependency, respectively, of the glutamate-induced increase in calcium ion concentration in seven- to eight-day-old rat cerebellar granule cells, as performed in the Comparative Experiment.
Figure 14:
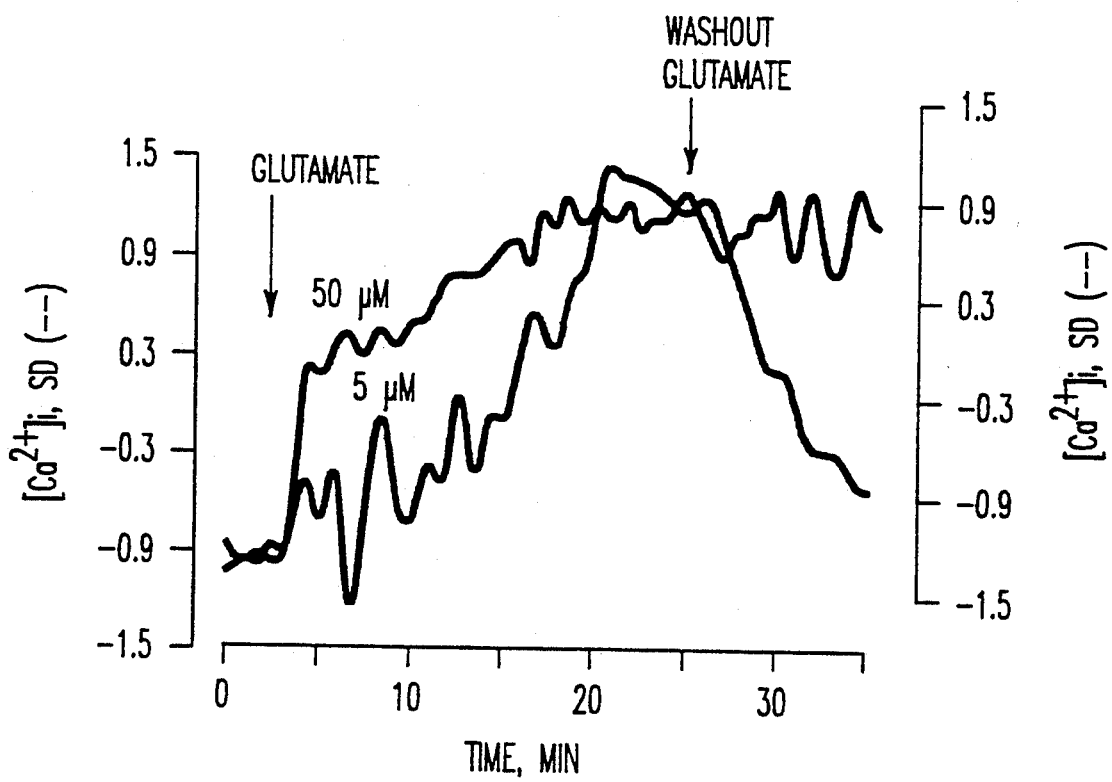
Figure 15C:
FIGS. 15A, 15B, 15C, 15D, 15E and 15F show the dynamic changes of calcium ion concentration and propidium iodide influx into neurons after a toxic dose of glutamate, as performed in the Comparative Experiment.
Figure 15F:
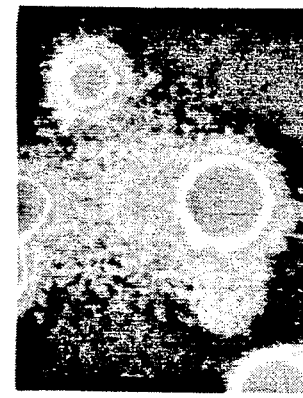
Figure 15B:
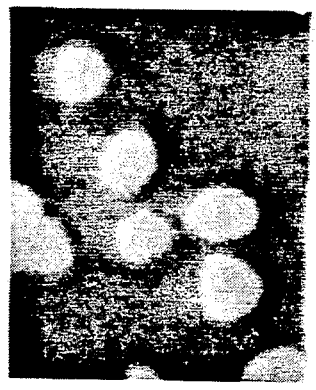
Figure 15E:
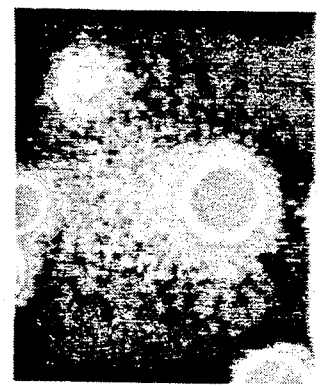
Figure 15A:
Figure 15D:
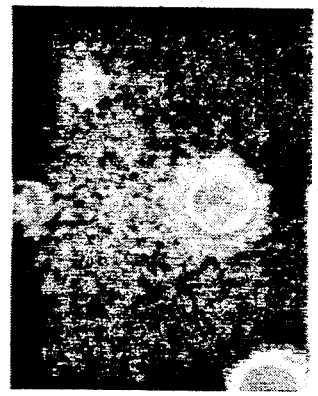

The glutamate-induced rise in calcium ion concentration during perfusion with glutamate in $Mg^{2+}$-free buffer is time-and dose-dependent, as shown in FIGS. 13 and 14. Perfusion with $Mg^{2+}$-free Locke's solution alone did not change basal calcium ion concentration (37±5 nM). However, in $Mg^{2+}$-containing buffer, neither 5 $\mu$M glutamate ($[Ca^{2+}]=52\pm2$ nM) or 50 $\mu$M glutamate ($[Ca^{2+}]=64\pm6$ nM) was able to induce consistent rises in $[Ca^{2+}]$, while the response to 500 $\mu$M glutamate ($[Ca^{2+}]=110\pm25$ nM) was markedly reduced under these conditions. Furthermore, perfusion with 1 $\mu$M dibenzocycloheptaneimine (MK-801) had no effect on basal $[Ca^{2+}]$. When started 1 min before application of glutamate, perfusion with 1 $\mu$M dibenzocycloheptaneimine suppressed all changes in $[Ca^{2+}]$ in response to concentrations of glutamate up to 500 $\mu$M.

Propidium iodide is a charged polar compound that only penetrates damaged cell membranes and interacts with nuclear DNA yielding a bright red fluorescent complex (Jones et al, *J. Histochem. Cytochem.*, 33:77-79 (1985)). The dynamic changes of calcium ion concentration and of propidium iodide neuronal influx after a toxic dose of glutamate are shown in FIG. 15. According to the images in FIG. 15, about 2 h after removal of the toxic concentration of glutamate, most cells show a further and larger increase in calcium ion concentration. About 10 min later, the first appearance of propidium iodide fluorescence is noted, indicating loss of viability.

The statistical analysis of the data was performed using conventional methods known to those in the art. For averaging of temporal curves the z transformation was used (mean subtraction and then division by the standard deviation [SD]). For the correlation between $[Ca^{2+}]$ and viability, the Spearman rank correlation test was performed. Finally, a one-way analysis of variance was used for dose-response curves and a two-way analysis of variance for the effects of additional treatments. All the statistical calculations were done using the corresponding routines of STATGRAF (version 2.1; Statistical Graphic Systems, Rockville, MD).

After receiving toxic doses of glutamate, the degree of alteration in the calcium ion concentration in cells is predictive of the loss of viability. This correlation is statistically very significant according to the Spearman test (R =0.88; P <0,005). In the same cells, the calcium concentration either in basal conditions, (i.e., before glutamate exposure) (R =0.45; P >0.10) or in steady-state conditions (at 20 min glutamate exposure) (R =0.67; P <0.05) did not correlate with the time of viability loss as well as post-glutamate levels did, showing that destabilization of $[Ca^{2+}]$ homeostasis in the post-glutamate period, and not basal calcium ion concentration, is a critical index of cell death.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the united states is:

1. A method for determining the concentration of two luminescence-affecting chemical species in a sample capable of emitting luminescent radiation, comprising the steps of:

(1) irradiating said sample with excitation radiation of sufficient energy to cause said sample to emit two pairs of independent luminescent emissions, each emission having an intensity, and for each one of said two pairs of independent luminescent emissions, each member of said pair having a common wavelength of excitation radiation or emission radiation and a different wavelength of excitation radiation or emission radiation, such that when said common wavelength is excitation radiation, said different wavelength is emission radiation, and when said common wavelength is emission radiation, said different wavelength is excitation radiation, (2) measuring the intensity of each of said two pairs of independent luminescent emissions within a period of time of from about one microsecond to one minute, (3) determining, for each of said two pairs of independent luminescent emissions, a ratio of one of said luminescent radiation emission intensities of said pair to the remaining one of said luminescent radiation emission intensities of said pair, and (4) correlating each ratio to concentrations of each of said two luminescence-affecting chemical species in said sample.

2. The method of claim 1, further comprising the step of:

(5) producing at least two images of said sample, each of said two images showing each of said concentrations of each of said two luminescence-affecting chemical species in said sample.

3. The method of claim 1, wherein said sample has at least one luminescent compound admixed therewith.

4. The method of claim 1, wherein said emissions are fluorescent emissions.

5. The method of claim 4, wherein said sample has at least two fluorescent compounds admixed therewith.

6. The method of claim 1, further comprising repeating measuring step (2) within a period of time of from 1 millisecond to one minute.

7. The method of claim 4, wherein said sample contains biological cells.

8. The method of claim 7, wherein each one of said luminescence-affecting chemical species affects the fluorescence of one of said fluorescent compounds, and said one of said luminescence-affecting chemical species and said one of said fluorescent compounds are selected from the group consisting of (a) fura-2 and $Ca^{2+}$, (b) Indo-1 and $Ca^{2+}$, (c) indo-1 and $Mg^{2+}$, (d) fluo-3 and $Ca^{2+}$, (e) fluorescein or a derivative thereof and pH, (f) a SNARF reagent and pH, (g) 2'7'-bis-(carboxyethyl)-5(6)-carboxyfluoresceine (BCECF) and pH, (h) cyclic adenosine monophosphate (cAMP) and a fluoresceine- and rhodamine--labelled cAMP-dependent protein kinase (F1CRhR), and (i) fluorescamine and a primary amine.

9. The method of claim 8, wherein said two luminescence-affecting chemical species are selected from the group consisting of (i) pH and $Ca^{2+}$ and (ii) cAMP and $Ca^{2+}$.

10. The method of claim 9, wherein said luminescence-affecting chemical species and said fluorescent compounds are selected from the group consisting of (i) pH and BCECF, and $Ca^{2+}$ and fura-2; and (ii) cAMP and F1CRhR, and $Ca^{2+}$ and fura-2.

11. A method for determining the concentration of two luminescence-affecting chemical species in a sample capable of emitting luminescent radiation, comprising the steps of:

(1) irradiating a sample having two luminescent substance/luminescence-affecting species complexes with excitation radiation of sufficient energy to cause each luminescent substance/luminescence-affecting species complex in the sample to emit a pair of independent luminescent emissions, each emission having an intensity, (2) measuring the intensity of each of the two pairs of independent luminescent emissions within a period of time of from about one microsecond to one minute, (3) determining, for each of the luminescent substance/luminescence-affecting species complexes, a ratio of one of the luminescent radiation emission intensities of the to the remaining one of the luminescent radiation emission intensities of the pair, and (4) correlating each ratio to concentrations of each of the two luminescence-affecting chemical species in the sample.

12. The method of claim 11, further comprising the step of:

(5) producing at least two images of said sample, each of said two images showing each of said concentrations of each of said two luminescence-affecting chemical species in said sample.

13. The method of claim 11, wherein said sample contains biological cells.

14. An apparatus for producing multiple luminescence ratio images, comprising:

(A) a light source providing a light beam of sufficient energy to electronically excite at least one luminescent compound in a sample, (B) a light filter positioned in the path of the light beam to filter out selected wavelengths of the light beam, (C) a dichroic mirror positioned in the path of the filtered light beam to reflect said filtered light beam in the direction of said sample, (D) a mounting platform for said sample positioned such that the reflected light beam strikes said sample so that said luminescent compound becomes electronically excited and produces luminescent emissions, (E) a detector positioned to receive the reflected luminescent emissions and having an electronic switching device for adjusting the sensitivity of said detector at least four times within a period of time of from about one microsecond to one minute.

15. The apparatus of claim 14, wherein said detector comprises (a) a lens to intercept and focus said reflected luminescent emissions, (b) a camera equipped with a photosensitive element positioned to intercept the focused luminescent emissions, and (c) means for augmenting electronic signals generated in the photosensitive element, electronically connected to said photosensitive element, wherein said electronic switching device of said detector is electronically connected to said photosensitive element.

16. The apparatus of claim 14, further comprising:

(F) one or more reflecting mirrors positioned to reflect the luminescent emissions from said sample.

* * * * *